(12) United States Patent
Roughead et al.

(10) Patent No.: US 9,192,179 B2
(45) Date of Patent: Nov. 24, 2015

(54) METHODS FOR PROMOTING GUT MICROBIOTA BALANCE

(75) Inventors: Zamzam (Fariba) Roughead, Plymouth, MN (US); Jalil Benyacoub, Lausanne (CH); Claudia Roessle, Morges (CH); Jennifer Rae Mager, St. Paul, MN (US); Julie Ann Swanson, Minneapolis, MN (US); Norman Alan Greenberg, New Hope, MN (US); Douglas Richard Bolster, Eden Prairie, MN (US); Clara Lucia Garcia Rodenas, Forel (CH); Florence Rochat, Montreux (CH)

(73) Assignee: Nestec S.A., Vevey (CH)

( * ) Notice: Subject to any disclaimer, the term of this patent is extended or adjusted under 35 U.S.C. 154(b) by 448 days.

(21) Appl. No.: 13/502,918

(22) PCT Filed: Nov. 11, 2010

(86) PCT No.: PCT/US2010/056321
§ 371 (c)(1),
(2), (4) Date: Jun. 7, 2012

(87) PCT Pub. No.: WO2011/060123
PCT Pub. Date: May 19, 2011

(65) Prior Publication Data
US 2012/0269865 A1    Oct. 25, 2012

Related U.S. Application Data

(60) Provisional application No. 61/260,495, filed on Nov. 12, 2009, provisional application No. 61/264,430, filed on Nov. 25, 2009, provisional application No. 61/394,805, filed on Oct. 20, 2010.

(51) Int. Cl.
| | | |
|---|---|---|
| *A61K 47/00* | (2006.01) | |
| *A61K 31/70* | (2006.01) | |
| *A23L 1/053* | (2006.01) | |
| *A23L 1/0528* | (2006.01) | |
| *A23L 1/29* | (2006.01) | |
| *A23L 1/308* | (2006.01) | |

(52) U.S. Cl.
CPC ............... *A23L 1/053* (2013.01); *A23L 1/0528* (2013.01); *A23L 1/296* (2013.01); *A23L 1/308* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,101,553 B2 * | 9/2006 | Haschke et al. | ............ 424/184.1 |
| 7,141,554 B2 | 11/2006 | Rochat et al. | |
| 2002/0044957 A1 | 4/2002 | Fuchs et al. | |
| 2003/0040492 A1 | 2/2003 | Haschke et al. | |
| 2004/0191234 A1 | 9/2004 | Haschke et al. | |
| 2004/0219157 A1 | 11/2004 | Rochat et al. | |
| 2005/0053641 A1 | 3/2005 | Rochat et al. | |

FOREIGN PATENT DOCUMENTS

| | | |
|---|---|---|
| CN | 1997290 | 7/2007 |
| CN | 101534656 | 9/2009 |
| EP | 1597978 | 11/2005 |
| EP | 1917969 | 5/2008 |
| EP | 2014181 | 1/2009 |
| WO | 0035303 | 6/2000 |
| WO | 2005107499 | 11/2005 |
| WO | 2007039596 | 4/2007 |

OTHER PUBLICATIONS

International Preliminary Report on Patentability PCT/US2010/056321 issue date May 15, 2012, 1 page.
International Search Report PCT/EP2010/056321 mailing date Mar. 2, 2011, 5 pages.
Written Opinion of the International Searching Authority PCT/EP2010/056321 mailing date Mar. 2, 2011, 6 pages.
Goetze, Oliver. Effect of a Prebiotic Misture on Intestinal Comfort and General Wellbeing in Health. British Journal of Nutrition (2008), 100, 1077-1085. 10 pages.
Watabe, Junko. Carbohydrate Fermentation in the Colon. J. Intest Bicrobiol. 2005:19:169-177. 10 pages.

* cited by examiner

*Primary Examiner* — Yunsoo Kim
(74) *Attorney, Agent, or Firm* — K&L Gates LLP

(57) ABSTRACT

The present disclosure relates to nutritional compositions comprising a fructo-oligosaccharide (FOS) in an amount of 35 to 44% by weight; a polysaccharide that is not a partially hydrolyzed guar gum such as, for example, an arabinogalactan in an amount of 50% to 38% by weight; and inulin in an amount of 12% to 24% by weight. The FOS and the polysaccharide may be present in a weight ratio of about 1:1. More specifically, the FOS and inulin may be present in a weight ratio of about 7:3. Also provided are methods of promoting gut microbiota balance and health. The methods include administering an effective amount of the nutritional composition to patients in need of same.

18 Claims, 28 Drawing Sheets

|  | SHIME 1 ctr wk1 | | | SHIME 2 ctr wk1 | | |
|---|---|---|---|---|---|---|
| AC | Conc. | stdev | Anova | Conc. | stdev | Anova |
| acetate | 26.0 | 2.1 | a | 29.6 | 1.8 | a |
| propionate | 17.7 | 1.1 | a | 17.7 | 1.5 | a |
| butyrate | 10.0 | 0.8 | a | 9.8 | 0.7 | a |
| total | 56.5 | 2.9 | a | 60.0 | 2.3 | a |
| | | | | | | |
| TC | Conc. | stdev | Anova | Conc. | stdev | Anova |
| acetate | 31.0 | 0.6 | a | 32.1 | 0.8 | a |
| propionate | 20.5 | 1.0 | a | 19.3 | 0.6 | a |
| butyrate | 10.0 | 0.5 | a | 10.2 | 0.5 | a |
| total | 64.6 | 1.5 | a | 64.7 | 1.5 | a |
| | | | | | | |
| DC | Conc. | stdev | Anova | Conc. | stdev | Anova |
| acetate | 36.2 | 1.0 | a | 33.7 | 4.5 | a |
| propionate | 20.4 | 1.1 | a | 17.3 | 2.6 | a |
| butyrate | 8.6 | 0.8 | a | 7.8 | 1.3 | a |
| total | 71.8 | 2.0 | a | 65.7 | 9.8 | a |

FIGURE 5A

|  | SHIME 1 ctr wk2 | | | SHIME 2 ctr wk2 | | |
|---|---|---|---|---|---|---|
| AC | Conc. | stdev | Anova | Conc. | stdev | Anova |
| acetate | 28.8 | 1.7 | a | 30.9 | 1.3 | a |
| propionate | 20.0 | 1.9 | a | 20.6 | 2.5 | a |
| butyrate | 9.8 | 1.0 | a | 9.9 | 1.0 | a |
| total | 61.6 | 1.4 | a | 64.4 | 5.0 | a |
| | | | | | | |
| TC | Conc. | stdev | Anova | Conc. | stdev | Anova |
| acetate | 32.7 | 0.9 | a | 32.1 | 3.9 | a |
| propionate | 21.3 | 2.0 | a | 20.6 | 3.8 | a |
| butyrate | 9.4 | 0.4 | a | 9.7 | 1.3 | a |
| total | 66.5 | 3.3 | a | 65.5 | 9.4 | a |
| | | | | | | |
| DC | Conc. | stdev | Anova | Conc. | stdev | Anova |
| acetate | 35.2 | 2.9 | a | 33.7 | 1.2 | a |
| propionate | 21.5 | 2.5 | a | 18.7 | 1.7 | a |
| butyrate | 8.8 | 0.8 | a | 8.4 | 0.3 | a |
| total | 71.3 | 6.6 | a | 65.9 | 4.0 | a |

FIGURE 5B

|  | SHIME 1 tr wk1 | | | SHIME 2 tr wk1 | | |
| --- | --- | --- | --- | --- | --- | --- |
| AC | Conc. | stdev | Anova | Conc. | stdev | Anova |
| acetate | 37.4 | 2.7 | a | 34.2 | 2.4 | a |
| propionate | 39.1 | 4.1 | a | 43.5 | 10.3 | a |
| butyrate | 15.6 | 3.4 | a | 12.4 | 1.2 | a |
| total | 93.3 | 5.5 | a | 91.7 | 11.8 | a |
| | | | | | | |
| TC | Conc. | stdev | Anova | Conc. | stdev | Anova |
| acetate | 35.0 | 1.2 | a | 36.0 | 4.5 | a |
| propionate | 34.8 | 11.6 | a | 40.1 | 17.2 | a |
| butyrate | 19.0 | 10.2 | a | 14.4 | 4.4 | a |
| total | 91.4 | 22.4 | a | 92.9 | 26.0 | a |
| | | | | | | |
| DC | Conc. | stdev | Anova | Conc. | stdev | Anova |
| acetate | 39.5 | 5.7 | a | 38.7 | 12.3 | a |
| propionate | 32.4 | 12.8 | a | 33.1 | 18.9 | a |
| butyrate | 15.3 | 9.0 | a | 11.0 | 4.2 | a |
| total | 95.1 | 29.5 | a | 88.5 | 37.3 | a |

FIGURE 5C

|  | SHIME 1 tr wk2 | | | SHIME 2 tr wk2 | | |
| --- | --- | --- | --- | --- | --- | --- |
| AC | Conc. | stdev | Anova | Conc. | stdev | Anova |
| acetate | 33.3 | 4.5 | a | 34.8 | 2.2 | a |
| propionate | 45.3 | 2.3 | a | 49.3 | 2.4 | a |
| butyrate | 19.0 | 7.2 | a | 13.7 | 1.5 | a |
| total | 99.2 | 5.5 | a | 98.9 | 5.6 | a |
| | | | | | | |
| TC | Conc. | stdev | Anova | Conc. | stdev | Anova |
| acetate | 38.1 | 1.5 | a | 42.1 | 2.8 | a |
| propionate | 50.7 | 0.8 | a | 56.9 | 1.4 | b |
| butyrate | 29.2 | 3.3 | a | 18.3 | 2.0 | b |
| total | 121.0 | 4.9 | a | 119.6 | 1.4 | a |
| | | | | | | |
| DC | Conc. | stdev | Anova | Conc. | stdev | Anova |
| acetate | 45.3 | 2.1 | a | 50.4 | 4.8 | a |
| propionate | 47.3 | 1.2 | a | 52.4 | 2.8 | a |
| butyrate | 24.8 | 2.9 | a | 16.7 | 1.5 | b |
| total | 128.7 | 0.8 | a | 128.1 | 6.9 | a |

FIGURE 5D

|  | SHIME 1 tr wk3 | | | SHIME 2 tr wk3 | | |
|---|---|---|---|---|---|---|
| AC | Conc. | stdev | Anova | Conc. | stdev | Anova |
| acetate | 33.8 | 2.5 | a | 35.2 | 4.3 | a |
| propionate | 48.1 | 7.7 | a | 48.3 | 6.4 | a |
| butyrate | 23.7 | 5.2 | a | 13.7 | 3.7 | b |
| total | 107.3 | 15.7 | a | 98.6 | 14.6 | a |
|  |  |  |  |  |  |  |
| TC | Conc. | stdev | Anova | Conc. | stdev | Anova |
| acetate | 37.7 | 0.9 | a | 41.3 | 3.0 | a |
| propionate | 48.3 | 2.2 | a | 51.0 | 2.5 | a |
| butyrate | 25.0 | 1.7 | a | 15.3 | 2.3 | b |
| total | 113.5 | 4.1 | a | 109.6 | 7.6 | a |
|  |  |  |  |  |  |  |
| DC | Conc. | stdev | Anova | Conc. | stdev | Anova |
| acetate | 44.1 | 2.8 | a | 54.4 | 4.9 | a |
| propionate | 47.3 | 1.1 | a | 49.6 | 1.6 | a |
| butyrate | 23.1 | 1.8 | a | 15.5 | 2.2 | a |
| total | 122.1 | 1.6 | a | 125.0 | 8.2 | a |

FIGURE 5E

METHODS FOR PROMOTING GUT MICROBIOTA BALANCE

CROSS REFERENCE TO RELATED APPLICATIONS

The present application is a National Stage of International Application No. PCT/US2010/056321, filed on Nov. 11, 2010, which claims priority to U.S. Provisional Patent Application No. 61/260,495, filed on Nov. 12, 2009, U.S. Provisional Patent Application No. 61/264,430, filed on Nov. 25, 2009, and U.S. Provisional Patent Application No. 61/394,805, filed on Oct. 20, 2010, the entire contents of which are being incorporated herein by reference.

BACKGROUND

The present disclosure is related to nutritional compositions comprising dietary fibers for promoting gut microbiota balance and health and methods of improving gut microbiota balance and health, which includes administering an effective amount of such composition.

It is well known that infection by pathogenic bacteria can be detrimental to health. Examples of these bacteria include *Clostridium perfringens, C. difficile, Salmonella* and other enteropathogens.

In the past, infection by these harmful bacteria has been allowed to proceed until it must be treated by antibiotics. The antibiotics have a good effect on harmful bacteria. However, they suffer from the problem that they also kill populations of intestinal bacteria that are not harmful and that aid digestion of food and provide other additional health benefits. These bacterial populations are often referred to as "friendly."

Gram-positive, non-motile, often branched anaerobic bacteria (*Bifidobacteria*) are one of the major genera of bacteria that make up the gut microbiota, the bacteria that reside in the colon. *Bifidobacteria* aid in digestion, are associated with a lower incidence of allergies and also prevent some forms of tumor growth. Other health benefits of *Bifidobacteria* include increased defense against pathogenic bacteria, stimulation of the immune system, and health benefits relating to the production of short chain fatty acids ("SCFAs"), as well as less abdominal sensitivity.

Prebiotics are non-digestible substances that can beneficially affect the host by selectively stimulating the growth of the gut microbiota. Fructo-Oligosaccharides ("FOS") are compounds for promoting the growth of *Bifidobacteria* and other beneficial gut microbiota, and have been extensively studied as prebiotics. FOS are short chain polymers of simple carbohydrates that do not behave like simple sugars in the body. FOS occur naturally in chicory, bananas, garlic, and certain other foods, and are, technically, a soluble fiber. It has been shown that FOS selectively support the proliferation of intestinal probiotics, especially the *Bifidobacteria*.

Oligofructose ("OF") is obtained from inulin, which is extracted from chicory using hot water. This yields a product with:

~92% inulin-type fructans (molecules with β-2,1 fructosyl-fructose glycosidic bonds);

Degree of Polymerization ("DP") ranging from 2-60 (avg of 10-12); and

~6-10% free sugars (fructose, glucose, and sucrose).

Further processing (partial enzymatic hydrolysis or separation procedures) can yield OF products. This can also increase purity by removing free sugars. All bonds in these products are in the β-2,1 configuration.

Alternatively, FOS is produced synthetically starting with a sucrose molecule. The fungal enzyme β-fructosidase is used to add fructose units with β-2,1 linkages in a process called transfructosylation. A limited number of other linkages are also formed by this process. The DP range is usually 2-4, and all start with a glucose residue.

The term inulin-type fructans ("ITF") refers to all linear fructans that contain β-2,1 fructosyl-fructose glycosidic bonds.

Product contains molecules with varying DP and proportion of glucose; generally described by the average DP, max DP, or range of DP.

Some ITF have a glucose as the starting unit ("GFn-type"), while others do not ("Fn-type")

ITF are not labeled uniformly in the literature, as there is no official standard. However, they can be categorized by DP:

Long chain=≥10 DP; and
Short chain=<10 DP.

Nomenclature for ITF is inconsistent in the literature. Some consider OF and FOS synonymous and are defined as ITF with DPmax<10. Others use FOS to describe short chain ITF (DP<10) that are synthesized from sucrose and have the GFn chemical structure and enzymatically attached fructose units. OF describes short chain molecules derived from inulin hydrolysis and can have either the GFn or the Fn structure.

PREBIO1™ additive, available from Nesté SA, is a unique prebiotic blend of the soluble fibers FOS and inulin, designed to support complete colonic health, in particular, proximal and distal colon health, to help maintain colonic integrity and to promote healthy gut microbiota. Formulas containing PREBIO1™ additive can also provide nutrition support for patients with gastrointestinal ("GI") compromise, such as chronic diarrhea/malnutrition, early enteral feeding, transition from TPN, short-bowel syndrome, chronic pancreatitis, malabsorption related to cancer treatment, HIV/AIDS, delayed gastric emptying, and cystic fibrosis.

The present disclosure satisfies the needs of the nutritional support industry by providing a composition with improved tolerance and increased prebiotic benefits compared to the PREBIO1™ additive, thereby providing a new composition that promotes gut microbiota balance and health of the individuals to which it is administered.

SUMMARY

The present disclosure now provides a novel nutritional composition that includes the combination of a FOS, a polysaccharide and inulin in relative amounts sufficient to provide nutrition when administered to an individual in need of the same. The composition provides a nutritional supplement to the individual's needs, and may be administered orally. Enteral administration for patients in need of tube feeding is also possible.

The composition generally comprises FOS in an amount of about 38% to about 44% by weight. The polysaccharide is typically an arabinogalactan, such as a gum and, in an embodiment, acacia gum ("AG"), and is present in an amount of about 38% to about 44% by weight. The inulin is present in an amount of about 12% to about 24% by weight. AG is a highly branched, high molecular weight molecule comprised of galactose, arabinose, rhamnose, and glucuronic acid units. It is slowly fermented compared to other soluble fibers and increases production of SCFA, and therefore may benefit the distal colon. See, Cherbut, et al., "Acacia Gum is a Bifidogenic Dietary Fibre with High Digestive Tolerance in Healthy Humans," *Microbial Ecology in Health and Disease*, 15(1):43-50 (2003). AG has a very high gastrointestinal tolerance, with up to 70 g/day causing no major side effects. See, Id. Low doses of AG (3 g/day) have been shown to be prebiotic and support the growth of *Bifidobacteria* when combined with 3 g/day FOS. See, Rochat, et al., "Method of Treating Irritable Bowel Syndrome," U.S. Pat. No. 7,141,554. Animal studies suggest an ability of AG to improve symptoms of diarrhea, and human trials have shown effects on normalizing bowel function. See, Wapnir, et al., "Gum Arabic Promotes Rat Jejunal Sodium and Water Absorption from Oral Rehydration Solutions in Two Models of Diarrhea," *Gastroenterology*, 112(6):1979-1985 (1997). See, also, Bliss, et al., "Supplementation with Gum Arabic Fiber Increases Fecal Nitrogen Excretion and Lowers Serum Urea Nitrogen Concentration Chronic Renal Failure Patients Consuming a Lowprotein Diet," *Am. J. Clin. Nutr.*, 63(3):392-398 (1996). See, also, Cherbut, et al. In addition, 5 g AG added to a meal has been shown to lower the glycemic response, and chronic consumption of 25 g/day has a lipid lowering effect. See, Ross, et al., "A Study of the Effects of Dietary Gum Arabic in Humans," *Am. J. Clin. Nutr.*, 37(3):368-375 (1983).

In one embodiment, the nutritional composition of the present disclosure comprises FOS and the arabinogalactan each present in an amount of about 40% to about 42% by weight; and inulin present in an amount of about 16% to about 20% by weight.

In an embodiment, the nutritional composition of the present disclosure comprises FOS and the arabinogalactan each present in an amount of about 41% by weight; and inulin present in an amount of about 18% by weight.

It is advantageous for the FOS and the arabinogalactan to be present in a weight ratio of about 44:38 to about 35:50, or about 42:40 to about 40:42, or about 1:1. Also, it is advantageous for the FOS and inulin to be present in a weight ratio of about 38:24 to about 44:12, or about 40:20 to about 42:16, or about 7:3.

In one embodiment of the nutritional composition of the present disclosure, the FOS is present in an amount of between 1.5-5.5 g/L, or about 4.12 g/L, the arabinogalactan such as, for example, AG, is present in an amount of 1.5-5.5 g/L, or about 4.12 g/L, and inulin is present in an amount of 0.5-2.5 g/L, or about 1.76 g/L. This composition may further comprise partially hydrolyzed guar gum ("PHGG") in an amount of up to 10 g/L. For example, PHGG may be provided in an amount from about 2 g/L to about 9 g/L. In one embodiment, PHGG may be present in an amount of 7 g/L. In another embodiment, PHGG may be present in an amount of 2.6 g/L. In another embodiment, PHGG is present in an amount of 5 g/L.

It should be noted that while guar gum is, chemically speaking, a polysaccharide, and while a PHGG might still be, at least in small part, a polysaccharide, the "polysaccharide" included in the presently claimed nutritional composition does not include PHGG. Instead, the PHGG may be added in addition to the polysaccharide such that, for example, AG and PHGG are not added together to obtain the 38-50% polysaccharide. Instead, PHGG may be added to the nutritional compositions in addition to the 38-50% polysaccharide.

In yet another embodiment, the nutritional composition of the present disclosure further comprises at least one insoluble fiber, such as a soy fiber, an outer pea fiber or both. In an embodiment, at least one insoluble fiber is a combination of a soy fiber and an outer pea fiber. The ratio between the soluble fiber of the composition, i.e., FOS, arabinogalactans such as AG, and inulin, and the insoluble fiber is between 1.5:1 and 1:1.5, or between 1.25:1 and 1:1.25, or about 1:1. In an embodiment, the FOS and AG are each present in an amount of between 2.5-3.5 g/L, and inulin is present in an amount of between 1.25-1.75 g/L, and the soy fiber and the outer pea fiber are each present in an amount of between 3.25-4.25 g/L. In yet another embodiment, the FOS and AG are present in an amount of about 3 g/L, inulin is present in an amount of about 1.5 g/L, and the soy fiber and the outer pea fiber are each present in an amount of about 3.75 g/L.

Another embodiment of the present disclosure relates to a dry powdered formulation comprising one of the nutritional compositions described herein. These powdered compositions may be made by a method that includes preparing one of the nutritional compositions disclosed herein as a liquid and then drying the liquid by spray drying, freeze drying or other drying techniques. It is also contemplated to add additional nutritional components or compositions to the liquid prior to drying to provide enhanced nutritional benefits to the powdered composition.

The present disclosure also relates to a number of different treatment methods that are designed to provide nutrition to various individuals. In general, the treatment methods promote gut microbiota balance and health by administering an effective amount of the nutritional composition of the present disclosure to an individual in need of such treatment.

Another method relates to improving patient tolerance to various medical treatments that lead to gastrointestinal tract disorders, such treatments including radiotherapy, chemotherapy, gastrointestinal surgery, anesthesia, the administration of antibiotic, analgesic drugs, or treatments for diarrhea. The method includes administering to such patients an effective amount of one of the nutritional compositions disclosed herein.

Another method relates to conferring systemic benefits, such as better catch-up growth, to hospitalized children. The method includes administering to such children an effective amount of one of the nutritional compositions disclosed herein.

Yet another method relates to reducing hospitalization time for patients. The method includes administering an effective amount of one of the nutritional compositions disclosed herein to a hospital patient, such as an elderly patient, to enable such patients to achieve acceptable nutrition levels and feeding goals with greater tolerance of such formulations to thus increase compliance with feeding turn improve the patient's condition to reduce hospitalization time.

Additional methods include treatments for minimizing negative evolutions of gut microbiota in an elderly individuals due to advancing age by administering an effective amount of one of the nutritional compositions disclosed herein to such individuals to enable such individuals to maintain healthy microbiota levels longer despite their increasing age while also decreasing *Clostridium* and increasing *Bifidobacteria*.

The present disclosure also provides a method for increasing butyrate production in a patient's colon, by administering an effective amount of one of the nutritional compositions disclosed herein to the patient to increase butyrate production compared to formulations that do not contain AG to produce cell proliferation and differentiation in the colon and to lower colon pH to inhibit the growth of pathogenic bacteria to provide anti-inflammatory benefits that help protect the patient's gut barrier.

Yet another method relates to boosting an individual's immune function by administering an effective amount of one of the nutritional compositions disclosed herein to decrease *Clostridium difficile* while T-cell function, gut-associated lymphoid tissue ("GALT") and secretory IgA ("sIgA") are enhanced to increase the individual's ability to resist sickness.

A method for improving organ transplant tolerance is also provided by administering to an individual who has received a transplant an effective amount of one of the nutritional compositions disclosed herein to impart therein specific colonizations that provide unique down regulation of the immune response and modulation of the inflammatory cytokines leading to decreased lean body mass, that GLP-1 and GLP-2 lead to increased insulin release. GLP-1 is insulinotrophic, but GLP-2 has trophic effects on the gut, e.g. enhanced intestinal crypt cell proliferation and villous height, see, Martin G R et al., "Nutrient-stimulated GLP-2 release and crypt cell proliferation in experimental short bowel syndrome," *Am. J. Physiol., Gastrointest., Liver Physiol.*, G431-G438 (2005), and a decrease in the imbalance between the T-helper cell (TH) 1 and TH 2 responses, see, Zhao Y, et. al., "Th1 and Th2 cytokines in organ transplantation: paradigm lost?," *Crit Rev Immunol.*, 1999; 19(2):155-72.

Yet another method relates to improving bone growth or preventing bone degradation in a patient in need of same, by increasing absorption of vitamins and nutrients in an individual's intestine and colon. The method includes administering to the patient an effective amount of one of the nutritional compositions disclosed herein to increase absorption of nutrients such as vitamin D, zinc, or calcium to assist in improving bone structure, growth and function.

Another method of the present disclosure relates to enhancing a patient's muscle mass by increasing absorption of vitamins and other nutrients in an individual's intestine and colon. The method includes administering to an individual who desires such enhanced muscle mass and increased absorption an effective amount of one of the nutritional compositions disclosed herein in order to specifically increase absorption of vitamins and minerals such as (but not limited to) vitamin D, folate, B12, magnesium, or calcium in the individual to assist in improvement of general well being, musculoskeletal health, mobility and cognitive health, prevent muscle mass depletion or improve muscle mass recovery.

The present disclosure also relates to a method of improving an individual's metabolism. The method includes administering to an individual who desires such improved metabolism an effective amount of one of the nutritional compositions disclosed herein in order to enhance micronutrient absorption, to improve bioavailability of such micronutrients.

The present disclosure also relates to a method of providing a fuller feeling or satiety so that the individual is able to have a better morning start, to avoid overeating, to decrease caloric intake or to provide sustained energy after administering of the composition.

Another method of the present disclosure relates to treating diabetes in a patient in need of such treatment. The method includes administering to such patient an effective amount of one of the nutritional compositions disclosed herein in order to decrease insulin resistance, to decrease blood glucose excursions or to lower CVD risk and to reduce azotemia in those with renal insufficiency.

The present disclosure also relates to the use of a polysaccharide, such as a gum including, for example, AG in a nutritional composition that includes a FOS and inulin for administration to an individual to provide nutrition thereto. The polysaccharide may be present in an amount effective to provide greater tolerance of such nutritional compositions when administered to the individual, with the polysaccharide, FOS and inulin being present in the amounts disclosed herein.

Another aspect of the present disclosure is the use of a polysaccharide, such as a gum including, for example, acacia gum for preparation of a nutritional composition for promoting gut microbiota balance and health in an individual. The nutritional composition may also include a FOS and inulin in amounts disclosed herein.

Additional features and advantages are described herein, and will be apparent from the following Detailed Description and the figures.

BRIEF DESCRIPTION OF THE FIGURES

FIGS. 5A-5E show data for the effects of Blend[1] (designated as "SHIME 1") and Blend[1+] (designated as "SHIME 2") on the production in the different colon vessels of the SHIME experiements. The data is presented per experiment week. Differences in ACFA concentrations among the colon compartments were evaluated by means of a one-way ANOVA, and individual means were compared using the Tukey's Test.

FIG. 13A represents data from experiments with Blend$^{1}$ and FIG. 13B represents data from experiments with Blend$^{1+}$. Where designated by *, the difference from the average of the control is statistically significant according to a T-test (p<0.05).

FIG. 14A represents data from experiments with Blend$^{1}$ and FIG. 14B represents data from experiments with Blend$^{1+}$. Where designated by *, the difference from the average of the control is statistically significant according to a T-test (p<0.05).

FIG. 15A represents data from experiments with Blend$^{1}$ and FIG. 15B represents data from experiments with Blend$^{1+}$. Where designated by *, the difference from the average of the control is statistically significant according to a T-test (p<0.05).

FIG. 16A represents data from experiments with Blend$^{1}$ and FIG. 16B represents data from experiments with Blend$^{1+}$. Where designated by *, the difference from the average of the control is statistically significant according to a T-test (p<0.05).

FIG. 17A represents data from experiments with Blend$^{1}$ and FIG. 17B represents data from experiments with Blend$^{1+}$. Where designated by *, the difference from the average of the control is statistically significant according to a T-test (p<0.05).

DETAILED DESCRIPTION

Definitions

Figure 1:
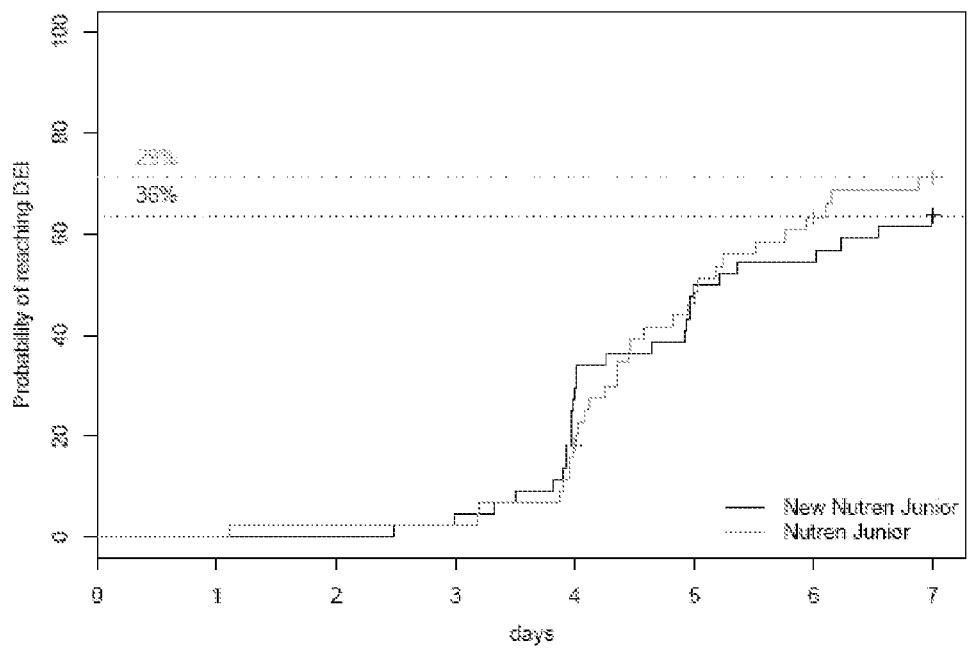
FIG. 1 shows time to reach the target caloric intake in hospitalized children in pediatric intensive care unit ("PICU") receiving mechanical ventilation and enteral feeding containing Blend[1+] (with probiotics NCC2461/NCC3001+prebiotics (PREBIO1™+AG)+DHA) or Blend[1] (without added pro- and prebiotics or DHA).

As used in this disclosure and the appended claims, the singular forms "a," "an" and "the" include plural referents unless the context clearly dictates otherwise. Thus, for example, reference to "an amino acid" includes a mixture of two or more amino acids, and the like.

As used herein, "about" is understood to refer to numbers in a range of numerals. Moreover, all numerical ranges herein should be understood to include all integer, whole or fractions, within the range.

As used herein the term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (wolfberry), hesperidine, lactowolfberry, lignan, lutein, lycopene, polyphenols, selenium, vitamin A, vitamin $B_{1}$, vitamin $B_{6}$, vitamin $B_{12}$, vitamin C, vitamin D, vitamin E, zeaxanthin, or combinations thereof.

As used herein, "complete nutrition" means nutritional products that contain sufficient types and levels of macronutrients (protein, fats and carbohydrates) and micronutrients to be sufficient to be a sole source of nutrition for the animal to which it is administered.

As used herein, "effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

As used herein, "incomplete nutrition" are nutritional products that do not contain sufficient levels of macronutrients (protein, fats and carbohydrates) or micronutrients to be sufficient to be a sole source of nutrition for the animal to which it is administered.

While the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, non-limiting examples of fish oils include docosahexaenoic acid ("DHA") and eicosapentaenoic acid ("EPA"). DHA and EPA may also be present from a non-fish oil source (e.g., algae, modified plants, etc.).

As used herein, "food grade micro-organisms" means micro-organisms that are used and generally regarded as safe for use in food.

As used herein, "long term administrations" are continuous administrations for more than 6 weeks.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

"Nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein the term "patient" is understood to include an animal, especially a mammal, and more especially a human that is receiving or intended to receive treatment, as it is herein defined.

As used herein, "phytochemicals" or "phytonutrients" are non-nutritive compounds that are found in many foods. Phytochemicals are functional foods that have health benefits beyond basic nutrition, and are health promoting compounds that come from plant sources. As used herein, "phytochemicals" and "phytonutrients" refers to any chemical produced by a plant that imparts one or more health benefit on the user. Phytochemicals can be administered by any means, including topically, enterally, and/or parenterally. As used herein, non-limiting examples of phytochemicals and phytonutrients include those that are i) Phenolic compounds which include Monophenols (such as: Apiole, Carnosol, Carvacrol, Dillapiole, Rosemarinol); Flavonoids (polyphenols) including Flavonols (such as: Quercetin, Gingerol, Kaempferol, Myricetin, Rutin, Isorhamnetin), Flavanones (such as: Hesperidin, Naringenin, Silybin, Eriodictyol), Flavones (such as: Apigenin, Tangeritin, Luteolin), Flavan-3-ols (such as: Catechins, (+)-Catechin, (+)-Gallocatechin, (−)-Epicatechin, (−)-Epigallocatechin, (−)-Epigallocatechin gallate (EGCG), (−)-Epicatechin 3-gallate, Theaflavin, Theaflavin-3-gallate, Theaflavin-3'-gallate, Theaflavin-3,3'-digallate, Thearubigins), Anthocyanins (flavonals) and Anthocyanidins (such as: Pelargonidin, Peonidin, Cyanidin, Delphinidin, Malvidin, Petunidin), Isoflavones (phytoestrogens) (such as: Daidzein (formononetin), Genistein (biochanin A), Glycitein), Dihydroflavonols, Chalcones, Coumestans (phytoestrogens), and Coumestrol; Phenolic acids (such as: Ellagic acid, Gallic acid, Tannic acid, Vanillin, Curcumin); Hydroxycinnamic acids (such as: Caffeic acid, Chlorogenic acid, Cinnamic acid, Ferulic acid, Coumarin); Lignans (phytoestrogens), Silymarin, Secoisolariciresinol, Pinoresinol and laricires-inol); Tyrosol esters (such as: Tyrosol, Hydroxytyrosol, Oleocanthal, Oleuropein); Stilbenoids (such as: Resveratrol, Pterostilbene, Piceatannol) and Punicalagins; ii) Terpenes (isoprenoids) which include Carotenoids (tetraterpenoids) including Carotenes (such as: α-Carotene, β-Carotene, γ-Carotene, δ-Carotene, Lycopene, Neurosporene, Phytofluene, Phytoene), and Xanthophylls (such as: Canthaxanthin, Cryptoxanthin, Zeaxanthin, Astaxanthin, Lutein, Rubixanthin); Monoterpenes (such as: Limonene, Perillyl alcohol); Saponins; Lipids including: Phytosterols (such as: Campesterol, beta Sitosterol, gamma sitosterol, Stigmasterol), Tocopherols (vitamin E), and omega-3, 6, and 9 fatty acids (such as: gamma-linolenic acid); Triterpenoid (such as: Oleanolic acid, Ursolic acid, Betulinic acid, Moronic acid); iii) Betalains which include Betacyanins (such as: betanin, isobetanin, probetanin, neobetanin); and Betaxanthins (non glycosidic versions) (such as: Indicaxanthin, and Vulgaxanthin); iv) Organosulfides which include Dithiolthiones (isothiocyanates) (such as: Sulphoraphane); and Thiosulphonates (allium compounds) (such as: Allyl methyl trisulfide, and Diallyl sulfide), Indoles, glucosinolates which include Indole-3-carbinol; sulforaphane; 3,3'-Diindolylmethane; Sinigrin; Allicin; Alliin; Allyl isothiocyanate; Piperine; Syn-propanethial-5-oxide; v) Protein inhibitors which include protease inhibitors; vi) Other organic acids which include Oxalic acid, Phytic acid (inositol hexaphosphate); Tartaric acid; and Anacardic acid; or combinations thereof.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125: 1401-1412. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y. et al., "Probiotics: how should they be defined?," *Trends Food Sci. Technol.*, 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostreptococcus, Pichia, Propionibacterium, Pseudocatenulatum, Rhizopus, Saccharomyces, Staphylococcus, Streptococcus, Torulopsis, Weissella*, or combinations thereof.

The terms "protein," "peptide," "oligopeptides" or "polypeptide," as used herein, are understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of proteins include dairy based proteins, plant based proteins, animal based proteins and artificial proteins. Dairy based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses.

As used herein, "short term administrations" are continuous administrations for less than 6 weeks.

As used herein, a "synbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein, a "tube feed" is a complete or incomplete nutritional product or composition that is administered to an animal's gastrointestinal system, other than through oral administration, including but not limited to a nasogastric tube, orogastric tube, gastric tube, jejunostomy tube ("J-tube"), percutaneous endoscopic gastrostomy ("PEG"), port, such as a chest wall port that provides access to the stomach, jejunum and other suitable access ports.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid and biotin) essential in minute amounts for normal growth and activity of the body and obtained naturally from plant and animal foods or synthetically made, pro-vitamins, derivatives, analogs.

Enteral Nutrition

Enteral nutrition is the preferred method of nutrient delivery for individuals who are unable to meet their nutritional needs orally. A standard formula is most commonly used in individuals with no specific medical concerns. These formulas have macro- and micronutrient contents which meet the recommendations for a healthy population and are generally well tolerated. In the past, fiber-free enteral formulas were preferred due to problems with tube clogging, as well as the notion that bowel rest was beneficial. As clogging problems due to fiber have since been mostly eliminated, it is now recognized that fiber can be included in such formulations in order to exert a number of beneficial physiological effects that are desirable for this population.

Direct Benefits of Fiber

Fiber increases the water content and bulk of alimentary contents, normalizing the progression of stool through the intestine. In this manner, dietary fiber contributes to improving the regularity of bowel movements, facilitating the generation of soft-formed stools, and improving ease and control of stool evacuation. Furthermore, soluble, viscous fibers have a number of metabolic benefits, including cholesterol-lowering effects. The presence of these fibers increases the viscosity of intestinal contents and can interfere with absorption of bile acids in the ileum, causing an increase in fecal bile acid loss. As a result, LDL cholesterol is removed from the blood by the liver and converted into bile acids to make up for this loss. Similarly, viscous fibers may also attenuate the glucose and insulin response to nutrient ingestion. These fibers can increase viscosity of the stomach, thus delaying gastric emptying. In addition, the increased viscosity of the chyme slows the rate of intestinal glucose absorption and reduces the need for insulin. By increasing viscosity of the stomach contents, these fibers also reduce the number of gastroesophageal reflux, regurgitation and vomiting episodes, which improves tolerance to the enteral feeds.

Indirect Benefits of Fiber

Approximately 100 trillion microorganisms are present in the typical adult intestine. The balance between beneficial and pathogenic bacteria is extremely important to maintain normal intestinal physiology, as this balance has direct effects on immune function and nutrient digestion and absorption. By definition, a prebiotic substance is "a selectively fermented ingredient that allows specific changes, both in the composition and/or activity in the gastrointestinal microbiota that confers benefits upon host wellbeing and health." This typically refers to an increase in *Bifidobacteria* and/or *lactobacilli*. Benefits of prebiotic substances (or prebiotics for short) include:

(1) an improvement in mucosal barrier function, helping to prevent translocation of bacteria to the blood stream;

(2) the promotion of beneficial and reduction of pathogenic bacterial subpopulations;

(3) the production of SCFA, e.g., butyrate, the major energy source for epithelial cells in the large intestine; SCFA also help regulate Na+ and water absorption; and (4) an improvement in host immunity, via interactions between intestinal immune cells and pathogenic bacteria.

Benefits of Dietary Fibers in Clinical Nutrition

Diarrhea and constipation are common complaints among patients on fiber-free enteral formulas. Fiber has been shown to normalize defecation frequency and transit time, and fiber may thus be added to formulas to promote regularity. A recent meta-analysis including 51 studies on fiber-supplemented enteral formulas found that fiber administration reduced the incidence of diarrhea and increased stool frequency when low, which is supportive of a moderating effect of fiber on bowel function. Likewise, a consensus panel of experts recommended the inclusion of fiber in the diets of all patients if no contraindication exists, based on benefits on diarrhea, constipation, and feeding tolerance. See, ESPEN, Guidelines 2006. Additional benefits of fiber include improved gut barrier function, colonic epithelial proliferation, enhanced fluid and electrolyte absorption, alleviated gastroesophageal reflux, regurgitation and vomiting, improving tolerance to the enteral feeds and benefits on glycemic control and serum lipid parameters. On the other hand, fiber supplementation has sometimes been reported to cause gastrointestinal side effects such as bloating and flatulence. Therefore, it is important to include fiber types and quantities with minimal gastrointestinal side effects.

Since it is well recognized that different fibers exert different health effects, the use of blends of fiber has become increasingly common. It is thought that blends more closely resemble a normal mixed diet and allow achievement of a range of physiological effects. There are currently no official recommendations for the ratio of soluble to insoluble fiber although it is estimated that in a mixed diet approximately 30% of the fiber consumed is soluble.

The Standard Tube Feeding fiber blend of Nestlé HealthCare Nutrition is specifically designed to maximize health benefits while optimizing gastrointestinal tolerance and ensuring acceptable viscosity and flow rates. The blend meets current recommendations by providing 15 g/L fiber of formula and a mixture of soluble and insoluble fibers. The soluble component of the fiber blend is designed to build and improve upon the existing scientific and brand equity of Nestlé's Branded Active Benefit, PREBIO1™ additive, which is a 70:30 blend of fructooligosaccharides (FOS) and inulin, which are low-viscous, soluble fibers obtained from chicory. These molecules are linear fructans which contain $\beta(2\text{-}1)$ fructosyl-fructose glycosidic bonds. Inulin (included at 1.5 g/L) refers to molecules with an average DP of $\geq 10$, while FOS (included at 3 g/L) has a lower DP and can be obtained as a hydrolysis product of inulin or by synthesis from fructose or fructose and glucose.

Both FOS and inulin have been extensively studied as prebiotics, with bifidogenic effects observed at doses as low as 4 g/d. Both are readily fermentable and appear to increase the production of propionate and butyrate, which is considered most beneficial for colonic health. These fibers have some bulking properties, and addition of FOS to an enteral formula has been shown to reduce constipation. Inulin and FOS also appear to benefit immune function. Inflammation and expression of proinflammatory cytokines were reduced in ulcerative colitis patients consuming 6 g/d of a FOS/inulin blend, and elderly nursing home patients receiving 8 g/d FOS observed an improvement in immune response as indicated by an increase in T lymphocytes. In addition, blends of these fibers (8 g/d and up) have been shown to enhance mineral absorption, e.g., calcium, magnesium, zinc or iron absorption, primarily in adolescents and postmenopausal women, which results in lowered blood pressure and better cardiovascular health, as well as better bone mineralization. To obtain the best results from FOS, however, daily intake should range between 5 and 10 grams a day as dosages above 15 grams may cause gas or intestinal cramping from excess *Bifidobacteria* populations. It has been found that GI tolerance due to gas production is improved when FOS/inulin blends are used compared to the use of either one alone.

The present disclosure provides a nutritional composition with the dose of these fibers below that shown to elicit gut discomfort while still confer prebiotic benefits. As discussed in the following section, the addition of AG in the nutritional composition of the present disclosure enables the use of low doses of inulin and FOS while increasing total fiber content and conferring a greater overall prebiotic benefit.

Standard Tube Feeding Blend

The present disclosure provides a new and improved composition comprising a 70:30 ratio of FOS and inulin (PREBIO1™) and a 1:1 ratio of FOS and AG. This provides a range of short (FOS), medium (inulin), and long chain (AG) fibers that are fermented at different rates, thus conferring benefits along the entire length of the colon.

AG, also known as Gum acacia, acacia gum, Gum Arabic or Indian gum, is a natural, non-viscous, soluble, fiber belonging to the complex arabinogalactan family. AG is a highly branched, high molecular weight molecule comprised of galactose, arabinose, rhamnose, and glucuronic acid units. This native substance has an average molecular weight between 300 and 800 kDa. It is composed for 95% of the dry weight of polysaccharides and for 1 to 2% depending on the species of proteins. AG is composed of three different fractions, i.e., 1% glycoprotein, 1-10% arabinogalactan-protein, and 90-99% arabinogalactan. AG is slowly fermented compared to other soluble fibers and increases production of SCFA, and therefore may benefit the distal colon. Low doses of AG (3 g/d) have been shown to be prebiotic when combined with 3 g/d FOS. Animal studies suggest an ability of AG to improve symptoms of diarrhea, and human trials have shown effects on normalizing bowel function. In addition, 5 g AG added to a meal has been shown to lower the glycemic response, and chronic consumption of 25 g/d has a lipid lowering effect.

Individuals generally have a very high gastrointestinal tolerance to AG, with the administration of up to 70 g/d causing no major side effects in healthy individuals. It has been found that the combination of FOS and AG in a 1:1 ratio, as provided in the composition of the present disclosure, reduces GI side effects such as bloating and stomach discomfort, in comparison to FOS alone, while at the same time conferring a synergistic prebiotic benefit. Thus, AG may provide partial substitution for FOS to offer prebiotic benefits without the tolerance issues. In addition, AG may also protect FOS from hydrolysis and help reducing the viscosity of soy fiber and other fibers such as outer pea fiber. It is believed that AG acts in a manner similar to an emulsifier to improve the performance of FOS in such compositions. Therefore, the addition of the highly complex, large molecular weight AG improves gut comfort while increasing the prebiotic benefit of the FOS fibers.

AG also provides a number of unexpected benefits in the formulations of the present disclosure. For example, it has been found that AG in the amounts described herein protects FOS from hydrolysis, thus retaining the FOS in a form that is active after administration to the individual. It is believed that AG also assists in maintaining formulation viscosity when other fibers such as soy fibers or pea fibers are present. Additional advantages of AG include its relatively low viscosity in water, its high solubility at room temperature, its neutral taste, color and odor, and its ability to improve mouth feel and enhance flavor release (when used with flavorants).

In the past, the rapid fermentation of inulin and FOS has been associated with excess gas and GI discomfort, thus limiting the dose of prebiotic fiber that can be added to products. Advantageously, the use of slowly fermented AG allows for delivery of a higher dose of prebiotic fibers without the associated GI intolerance. In addition, the use of a ratio of AG and FOS in the ratio of about 1:1 has been shown to promote a synergistic prebiotic effect as well as enhanced gastrointestinal tolerance, thus making this combination of soluble fibers ideal for addition to enteral formulas.

One of the major problems in enteral nutrition is the occurrence of diarrhea and other gastrointestinal side effects during nutrition. There are reports about the diarrhea rate between 2% and 67% of patients receiving enteral nutrition. See, Patti Eisenberg, "An Overview of Diarrhea in the Patient Receiving Enteral Nutrition," *Gastroenterology Nursing,* 25(3):95-104 (2002).

The composition of the present disclosure uses strong prebiotic fibers with a range of molecular weights (very small to very large) and fermentation rates (fast to slow), which allows for SCFA production and prebiotic effects to be maintained along the entire length of the colon.

The amounts of FOS, inulin and AG can vary provided that they fall within the claimed ratios. As noted herein, amounts of FOS or AG can each be within the range of 1.5 to 10 g/L but may also be between 3 and 5.5 g/L. Inulin can range between 0.5 and 5 g/L but may also be between 1 and 2.5 g/L. These amounts used within the claimed ratios are well tolerated by individuals to whom the compositions are administered.

In another embodiment, the composition of the present disclosure further comprises insoluble outer pea fiber. Outer pea fiber is an insoluble fiber obtained from pea hulls and can be included at an amount of between 5 and 10 g/L, or between 7 and 8 g/L, or about 7.5 g/L. Outer pea fiber is primarily composed of arabinose-rich hemicelluloses, cellulose, and pectic substances, such as uronic acid. Addition of 4 g/d pea hull fiber to the diet of elderly institutionalized residents significantly increased bowel frequency and decreased need for laxative use (prune puree administration) compared to baseline. It has also been shown to increase stool weight in humans and animals. Addition of pea hull fiber (10 g) to a meal has also been found to reduce postprandial serum cholesterol levels.

Addition of insoluble fibers such as outer pea fiber, soy protein, cellulose, or hemicellulose provides benefits on regularity and fecal bulking. To provide efficacious doses of the prebiotic fibers and to optimize GI tolerance and technical performance, the ratio of soluble/insoluble fiber may be set at 50:50. One embodiment of such a composition is shown in Table 1. The amount of fiber offered by the blend in a complete feeding meets the recommendations set by several professional associations such as:

(a) European Society for Parenteral and Enteral Nutrition ("ESPEN"): Patients with normal gut function, including post-surgical patients, may benefit from added fiber; 10-15 g fiber/L is an appropriate minimal amount;

(b) Institute of Medicine ("IOM") and American Dietetic Association ("ADA"): 14 g fiber/1000 kcal; and (c) American Diabetes Association ("ADA"): 15-25 g fiber/1000 kcal.

TABLE 1

Composition of the Standard Tube Feeding Blend
(adult and pediatric formula)*

| Fiber Type | Amount (g) in 1 L | Amount (g) in 1.5 L (complete feeding) |
| --- | --- | --- |
| FOS | 3 | 4.5 |
| Inulin | 1.5 | 2.25 |
| Acacia Gum | 3 | 4.5 |
| Outer Pea Fiber (source of cellulose, hemicellulose, and pectin) | 7.5 | 11.25 |
| Total | 15 | 22.5 |

*Assuming isocaloric formula (1.0-1.2 Kcal/mL)

Renal Fiber Blend

Patients with end-stage renal disease suffer from digestive disturbances, especially constipation. Approximately 50% of patients with end-stage renal disease suffer from constipation. See, Murtagh F E M, Addington-Hall J, Higginson I J. The Prevalence of Symptoms in End-Stage Renal Disease: A Systematic Review. Advances in Chronic Kidney Disease 2007; 14(1):82-89. PHGG is a unique, water-soluble dietary fiber that is extracted from guar gum. The original high viscosity of guar gum is nearly eliminated after hydrolysis, making it an ideal addition to liquid foods and nutritional formulas. There is data to support for the benefit of PHGG for bowel regularity, and constipation in particular. Many of the beneficial effects of PHGG are likely due to its complete fermentation in the colon, which produces significantly more butyrate than other soluble fibers. See, Velazquez M, Davies C, Marett R, Slavin J, Feirtag J. Effect of oligosaccharides and fibre substitutes on short chain fatty acid production by human faeca microflora. Anaerobe 2000; 6(2):87-92. As is the case with other soluble fibers that are rapidly fermented in the proximal colon, PHGG does not significantly increase stool weight. However, a number of studies have shown that PHGG is beneficial in normalizing bowel function, preventing or alleviating both diarrhea and constipation, especially in patients receiving enteral nutrition and other high risk populations. See, Slavin J L, Greenberg N A. 2003. Partially Hydrolyzed Guar Gum: Clinical Nutrition Uses. Nutrition; 19:549-552.

In a randomized, double blinded clinical trial, the influence of a soluble fiber, PHGG, on diarrhea rate in medical and surgical patients, was evaluated. Thirty of the 100 patients received total enteral nutrition ("TEN") following upper gastrointestinal surgery, 70 patients received a supplemental enteral nutrition of 1000 ml/d. Diarrhea occurred in 15 of the fiber free fed patients (30%) and in 6 of the fiber fed patients (12%) (P<0.05). In the fiber free diet group, there were 40.6 days noted where patients suffered from diarrhea, and 10.2 days were noted in the supplemented group (P<0.05, P<0.05). Discharge of enteral nutrition because of GI side effects was significantly more often in the fiber free group of patients who received TEN than in supplemented group. Use of PHGG lowered the rate of diarrhea occurrence in patients with total as well as supplemental enteral nutrition. Moreover, when diarrhea occurred in patients with fiber supplemented enteral nutrition, the duration was shorter.

In a study of long term care residents with constipation managed by enemas, daily supplementation with PHGG (18 g) resulted in a significant decrease in enema requirements in residents with higher enema usage at baseline. See, Soriano C V, Hibler K D, Maxey K I. Long-term fiber intervention program: reduction in enema use at a developmental care facility. Journal of the American Dietetic Association 2000S; 100(9):A82. In addition, PHGG (8-12 g per day) decreased the occurrence of constipation and significantly reduced laxative use in elderly nursing home residents who had been taking laxatives on a daily basis. See, Patrick P, Gohman S, Marx S, DeLegge M, Greenberg N. Effect of Supplements of Partially Hydrolyzed Guar Gum on the Occurrence of Constipation and Use of Laxative Agents. Journal of the American Dietetic Association 1998; 98(8):912-914. Similarly, the daily intake of 11 g of PHGG increased the frequency of bowel movements of women with constipation. See, Takahashi H, Yang S, Hayaski C, Kim M, Yamanaka J, Yamamoto T. Influence of partially hydrolyzed guar gum on constipation in women. Journal of Nutritional Science and Vitaminology 1994; 40:251-259. PHGG has also been shown to reduce symptoms of irritable bowel syndrome, as well as increase production of *Bifidobacterium* in the gut.

Moreover, the use of PHGG has also been shown to alleviate abdominal pain and improve bowel habits in adults with Irritable Bowel Syndrome ("IBS"). The majority of subjects in that study had constipation-predominate IBS. Subjects who received 5 g per day of PHGG reported greater subjective improvement compared to subjects who received wheat bran. See, Parisi G, Zilli M, Miani M et al. High-fiber diet supplementation in patients with irritable bowel syndrome (IBS): a multicenter, randomized, open trial comparison between wheat bran diet and partially hydrolyzed guar gum (PHGG). Dig Dis Sci 2002; 47(8):1697-704.

A number of compositions have been developed. As used herein, the composition referred to as "Renal Fiber Blend" is not intended to be limited to renal patients; it is intended to for those patient groups that can benefit from such a blend. For example, the Renal Fiber Blend also confers benefits for glycemic control and therefore is intended, in an embodiment, for patients with acute or chronic renal failure, who also often have stress-induced hyperglycemia or diabetes mellitus. Alternatively, the Renal Fiber Blend, since it confers glycemic benefits, is also intended, in an embodiment, for patients with hyperglycemia or diabetes mellitus without acute or chronic renal failure. In one embodiment, the composition of the present disclosure is a Renal Fiber Blend that further comprises PHGG. In an embodiment, the Renal Fiber Blend of the present disclosure comprises 3-5.5 g/L FOS, 1-2.5 g/L Inulin, 3-5.5 g/L AG, and 0-10 g/L PHGG.

In another embodiment, the Renal Fiber Blend of the present disclosure comprises 4.12 g/L FOS, 1.76 g/L Inulin, 4.12 g/L AG, and 7 g/L PHGG.

In yet another embodiment, the Renal Fiber Blend of the present disclosure comprises 4.12 g/L FOS, 1.76 g/L Inulin, 4.12 g/L AG, and 5 g/L PHGG.

In a further embodiment, the Renal Fiber Blend of the present disclosure comprises 4.12 g/L FOS, 1.76 g/L Inulin, 4.12 g/L AG, and 2.6 g/L PHGG.

In a further embodiment, the Renal Fiber Blend of the present disclosure comprises 4.0 g/L FOS, 1.76 g/L Inulin, and 4.0 g/L AG.

The nutritional compositions of the present disclosure may be prepared in liquid form. While water is the most common carrier for the other components, it is also envisioned to add the compositions to other liquids such as milk, fruit juice, coffee, tea or other beverages when such compositions are orally administered. Water is typically used for other enteral formulations.

The present disclosure also provides dry powdered formulations. These powdered formulations can be made by combining dry powdered ingredients or they can be made from one of the liquid nutritional compositions described herein. Typically, the powdered formulations are prepared by drying liquid nutritional compositions using spray drying, freeze drying or other drying techniques. If desired, other nutritional components or compositions can be added to the liquid prior to drying to provide enhance nutritional benefits to the powdered formulation. Such powdered formulations have a much greater shelf life and can be packaged for storage and transport for future use. At that time, the powdered formulations can be reconstituted with water or other fluids and then administered to the individual orally. The powdered formulation can be packaged in various containers, including those for bulk provision of such powdered formulations for adding to a liquid in a glass, bottle or other fluid containing vessel, or a single serving can be provided with the powder present in a container to which water or other fluids can be added to form the liquid for oral administration.

It is also contemplated that various conventional additives can be included in the liquid formulations of the present disclosure. For example, various flavorants, vitamins, minerals, antioxidants, preservatives or health benefit additives can be including in conventional amounts for their conventional purposes.

The compositions of the present disclosure can also be administered to individuals to increase probiotic stability. This benefit is particularly useful for powdered products, such that the powdered nutritional compositions can be reconstituted when the individual desires to consume the product to assist in maintaining probiotic stability.

The nutritional compositions of the present disclosure are generally used to promote gut microbiota health. Experimental data have shown that the nutritional composition of the present disclosure is well tolerated when provided enterally. In particular, the present nutritional compositions provide improved tolerance compared to PREBIO1™ as well as increased prebiotic benefits.

The composition of the present disclosure may be included as a partial or complete nutritional composition for use in enteral formulations that are administered for providing nutrition to HIV, Intensive Care Unit ("ICU") and pediatric patients as well as for improving gut health. It has been found that catch up weight gain is improved in such patients, most likely due to the improved tolerance of the compositions. It is also believed that the individual's immunity is boosted due to the improved microbiotic balance that is achieved after administration of the compositions.

The nutritional composition of the present disclosure may also be used to improve tolerance of various treatments that lead to GI disorders such as radiotherapy, chemotherapy, antibiotics, diarrhea treatments, gastrointestinal surgery, anesthesia, and analgesic drugs. The nutritional composition may also confer systemic benefits such as better catch-up growth in hospitalized children.

The nutritional compositions of the present disclosure can also be administered to assist patients in driving of Na/H$_2$O or mineral absorption in their intestines as well as to normalize transit time. These improvements in improving gut function also leads to a reduction in the side effects of various drugs that are administered for different treatments as such drugs are more efficiently eliminated from the individual. It is believed that these improvements are at least in part due to the ability of AG to provide a greater amount of butyrate in the patient's intestines. AG provides much greater amounts of butyrate compared to pectin, wheat bran, ispaghula or cellulose. In contrast, FOS primarily produces acetates rather than butyrates and acetates are metabolized by the liver. Inulin and PHGG also produce butyrates. Butyrates are desirable because they are the primary fuel for colon cells to produce cell proliferation. Butyrates also lower colon pH to inhibit the growth of pathogenic bacterial. This results in anti-inflammatory benefits that help protect the gut barrier.

For elderly patients, e.g., those over 65 years of age, the administration of the nutritional compositions of the present disclosure enable such patients to achieve acceptable nutrition levels and feeding goals with greater tolerance of such formulations. For hospitalized patients, the achievement of feeding goals and the provision of adequate nutrition typically leads to a decreased length of hospital stay, increased compliance with feeding requirements, and decreased complications such as diarrhea or constipation. The decreased hospital stays leads to decreased costs both to the patient as well as to the insurer.

The administration of the nutritional compositions of the present disclosure also minimizes the negative evolution of gut microbiota due to increased age of the individual. This enables individuals who receive such compositions to maintain healthy microbiota levels longer despite their increasing age. In addition, *Clostridium* is decreased while *Bifidobacteria* are increased.

The administration of the present nutritional compositions disclosed herein can also boost an individual's immune system. In particular, *Clostridium difficile* is decreased while T-cell function and GALT are increased. The individual's adaptive immunity sIgA and innate immunity are increased, such that the individual's ability to resist sickness increases. The specific colonizations that are imparted by the present compositions provide unique upregulation such that inflammatory cytokine leads to decreased lean body mass, GLP-1 and GLP-2 lead to increase insulin resistance, and the TH1/TH2 imbalance is reduced. It is believed that these benefits will lead to better transplant tolerance in such individuals.

Yet another method relates to improving bone growth or preventing bone degradation in a patient in need of same by increasing absorption of vitamins and nutrients in an individual's intestine and colon. The method includes administering to the patient an effective amount of one of the nutritional compositions disclosed herein to increase absorption of nutrients such as vitamin D, zinc or calcium to assist in improving bone composition and function.

Another method of the present disclosure relates to enhancing a patient's muscle mass by increasing absorption of nutrients in an individual's intestine and colon. The method includes administering to an individual who desired such enhanced muscle mass and increased absorption an effective amount of one of the nutritional compositions disclosed herein in order to specifically increase absorption of nutrients such as folates, vitamin D, magnesium or B12, in the individual to assist in muscle growth, prevent muscle mass depletion or improve muscle mass recovery.

An individual's metabolism can be improved by administering an effective amount of one of the nutritional compositions disclosed herein. This enables the individual to enhance micro-nutrient absorption, to improve bioavailability of such micro-nutrients, or provide greater caloric uptake. This can provide a number of advantages in that the individual is able to have a better morning start with such improved absorption. Furthermore, this can also be used to treat obesity in that the individual that receives the composition will have a fuller feeling or satiety to avoid overeating. This also can lead to a decrease in caloric intake while also providing sustained energy so that the individual may be able to partake in exercising or other activities that will burn calories after administering of the composition.

The compositions are also useful in treating diabetes in a patient in need of such treatment. The administering of one of the nutritional compositions disclosed herein can reduce insulin resistance, decrease blood glucose excursions or lower CVD risk.

Exemplary Embodiments

One embodiment of the present disclosure is a nutritional composition for administration to an individual including a fructo-oligosaccharide (FOS) in an amount of 35 to 44% by weight; a polysaccharide in an amount of 38% to 50% by weight; and inulin in an amount of 12 to 24% by weight. The FOS and polysaccharide may be present in a weight ratio of 62:38 to 38:62, and the FOS and inulin may be present in a weight ratio of 82:18 to 58:42. In a further embodiment, the FOS is 40 to 42% by weight. In a further embodiment, the FOS is about 41% by weight. In a further embodiment, the polysaccharide is AG. In a further embodiment, the polysaccharide is 40 to 50% by. In a further embodiment, polysaccharide is about 41% by weight. In a further embodiment, the AG is 40 to 42% by weight. In a further embodiment, AG is about 41% by weight. In a further embodiment, the inulin is 15 to 21% by weight. In a further embodiment, the inulin is 18% by weight. In a further embodiment, nutritional composition comprises: a (FOS) in an amount of 40 to 42% by weight; AG in an amount of 40% to 42% by weight; and inulin in an amount of 15 to 21 by weight. In a further embodiment, the nutritional composition comprises: a (FOS) in an amount of 41% by weight; a AG in an amount of 41% by weight; and inulin in an amount of 18% by weight. In a further embodiment, the FOS and polysaccharide are present in a weight ratio of 55:45 to 45:55. In a further embodiment, the FOS and polysaccharide are present in a weight ratio of about 1:1. In a further embodiment, the FOS and inulin are present in a weight ratio of 76:24 to 64:36. In a further embodiment, the FOS and inulin are present in a weight ratio of 7:3. In a further embodiment, the polysaccharide is an arabinogalactan and the FOS is present in an amount of between 3-5.5 g/L, the arabinogalactan is present in an amount of 3-5.5 g/L and inulin is present in an amount of 1-2.5 g/L. In a further embodiment, the nutritional composition further comprises up to 10 g/L of (PHGG). In a further embodiment, the arabinogalactan is AG and the FOS and AG are each present in an amount of 4.12 g/L, inulin is present in an amount of 1.76 g/L and PHGG is present in an amount of 7 g/L. In a further embodiment, the arabinogalactan is AG and the FOS and AG are each present in an amount of 4.12 g/L, inulin is present in an amount of 1.76 g/L and PHGG is present in an amount of 5 g/L. In a further embodiment, the arabinogalactan is AG and the FOS and AG are each present in an amount of 4.12 g/L, inulin is present in an amount of 1.76 g/L and PHGG is present in an amount of 2.6 g/L. In a further embodiment, the (FOS) in an amount of 35% by weight; a polysaccharide in an amount of 50% by weight; and inulin in an amount of 15% by weight. In a further embodiment, the (FOS) in an amount of 35% by weight; AG in an amount of 50% by weight; and inulin in an amount of 15% by weight.

Again, it should be noted that while guar gum is, chemically speaking, a polysaccharide, and while a PHGG might still be, at least in small part, a polysaccharide, the "polysaccharide" included in the presently claimed nutritional composition does not include PHGG. Instead, the PHGG may be added in addition to the polysaccharide such that, for example, AG and PHGG are not added together to obtain the 38-50% polysaccharide. Instead, PHGG may be added to the nutritional compositions in addition to the 38-50% polysaccharide.

In an embodiment, the nutritional composition further comprises at least one insoluble fiber in an amount effective to enhance digestive function in the individual, wherein the at least one insoluble fiber is a soy fiber, an outer pea fiber or a combination thereof. In a further embodiment of the nutritional composition the soluble fiber and insoluble fiber are present in a ratio of between 1.5:1 and 1:1.5, and the FOS and AG are present in a total amount of between 2.5-3.5 g/L, the inulin is present in an amount of between 1.25-1.75 g/L, and the soy fiber and the outer pea fiber are each present in an amount of between 3.25-4.25 g/L. In a further embodiment of the nutritional composition the soluble fiber and insoluble fiber are present in a ratio of 1.25:1 and 1:1.25. In a further embodiment of the nutritional composition the soluble fiber and insoluble fiber are present in a ratio of 1:1. In a further embodiment of the nutritional composition the FOS and AG are present in a total amount of about 3 g/L. In a further embodiment of the nutritional composition the inulin is present in an amount of about 1.5 g/L. In a further embodiment of the nutritional composition the soy fiber and the outer pea fiber are each present in an amount of about 3.75 g/L.

In an embodiment, the nutritional composition further comprises antioxidants.

In an embodiment, the nutritional composition further comprises fish oils or nonmarine oils such as algae.

In an embodiment, the nutritional composition further comprises DHA, EPA or combinations thereof.

In an embodiment, the nutritional composition further comprises Vitamins, Minerals or combinations thereof.

In an embodiment, the nutritional composition further comprises phytonutrients.

In an embodiment, the nutritional composition further comprises protein.

In an embodiment, the nutritional composition further comprises fat.

In an embodiment, the nutritional composition further comprises probiotics.

In an embodiment, the nutritional composition is a dry powdered formulation. In another embodiment, the nutritional composition is made by preparing one of the compositions as a liquid and drying the liquid composition by one of the processes known in the art, including spray drying, freeze drying or other drying techniques to produce a dry powdered composition. In a further embodiment additional nutritional components or compositions to the liquid prior to drying to provide enhance nutritional benefits to the powdered composition. In a further embodiment, a nutritional composition is obtained by reconstituting one of the dry powdered formulations of claims 35 to 37 by combining the formulation with a liquid.

In an embodiment, the nutritional composition is a complete nutritional. In an embodiment, the nutritional composition is an incomplete nutritional.

In an embodiment, the nutritional composition is used in a method of promoting gut microbiota balance and health. The method includes an effective amount of the nutritional composition to an individual who can benefit from such treatment.

In an embodiment, the nutritional composition is used in a method of improving patient tolerance to various medical treatments that lead to gastrointestinal tract disorders, such treatments including radiotherapy, chemotherapy, gastrointestinal surgery, anesthesia, the administration of antibiotics, analgesic drugs or treatments for diarrhea. The method includes administering to such patients an effective amount of the nutritional composition.

In an embodiment, the nutritional composition is used in a method for conferring benefits such as better catch-up growth, to children. The method includes administering to such children an effective amount of the nutritional composition.

In an embodiment, the nutritional composition is used in a method of reducing hospitalization time for patients. The method includes administering an effective amount of the nutritional composition to a hospital patient, to enable such patients to achieve acceptable nutrition levels and feeding goals with greater tolerance of such formulations to thus increased compliance with feeding requirements, and decreased complications such as diarrhea or constipation to in turn improve the patient's condition to thus reduce hospitalization time. In a further embodiment, the patient is adult and elderly.

In an embodiment, the nutritional composition is used in a method for minimizing negative evolutions of gut microbiota in an elderly individual due to advancing age by administering an effective amount of the nutritional composition to such individuals to enable such individuals to maintain healthy microbiota levels longer despite their increasing age. In a further embodiment, the method comprises decreasing *Clostridium*. In a further embodiment, the method comprises increasing *Bifidobacteria*.

In an embodiment, the nutritional composition is used in a method for increasing butyrate production in a patient's colon. The method includes administering an effective amount of the nutritional composition to the patient to increase butyrate production compared to formulations that do not contain AG to produce cell proliferation in the colon and to lower colon pH to inhibit the growth of pathogenic bacteria. In a further embodiment, the method leads to anti-inflammatory benefits that help protect the patient's gut barrier. In a further embodiment, the method leads to better mineral absorption. In a further embodiment, the method leads to a normalization of gastrointestinal transit time. In a further embodiment, the method leads to decrease in diarrhea. In a further embodiment, the method leads to a decrease in constipation.

In an embodiment, the nutritional composition is used in a method for boosting an individual's immune system. The method includes to an individual who desires to stimulate their immune system an effective amount of the nutritional composition. In a further embodiment, the stimulated immune system decreases pathogenic microorganisms, such as *Clostridium difficile*. In a further embodiment, the stimulated immune system comprises improved T-cell function. In a further embodiment, the stimulated immune system comprises improved GALT function. In a further embodiment, the stimulated immune system comprises enhanced sIgA production. In a further embodiment, the stimulated immune system increases the individual's ability to resist illness.

In an embodiment, the nutritional composition is used in a method for improving organ transplant tolerance by administering to an individual who has received a transplant an effective amount of the nutritional to impart therein specific colonizations that provide unique down regulation. In a further embodiment, the upregulation leads to decreased inflammatory cytokine that leads to increased lean body mass. In a further embodiment, the upregulation leads to increased insulin release through GLP-1 and GLP-2. In a further embodiment, the upregulation leads to decreased TH1/TH2 imbalance.

In an embodiment, the nutritional composition is used in a method for improving bone growth or preventing bone degradation in a patient in need of same by increasing absorption of vitamins and nutrients in an individual's intestine and colon. The method includes administering to the patient an effective amount of one of the nutritional compositions disclosed herein to increase absorption of nutrients such as vitamin D, zinc or calcium to assist in improving bone composition and function.

Another method of the present disclosure relates to enhancing a patient's muscle mass by increasing absorption of nutrients in an individual's intestine and colon. The method includes administering to an individual who desires such enhanced muscle mass and increased absorption an effective amount of one of the nutritional compositions disclosed herein in order to specifically increase absorption of nutrients such as calcium, vitamin D, folates, magnesium or B12, in the individual to assist in muscle growth, prevent muscle mass depletion or improve muscle mass recovery.

In an embodiment, the nutritional composition is used in a method of increasing absorption of vitamins and nutrients in an individual's intestine and colon. The method includes administering to an individual who desires such increased adsorption an effective amount of the nutritional composition in order to specifically increase absorption of vitamins or calcium and other minerals or vitamins and minerals in the individual. In a further embodiment, the vitamins are vitamin D, folates, B12, etc. In a further embodiment, the minerals are at least magnesium or calcium. In a further embodiment, the method assists in muscle growth. In a further embodiment, the method prevents muscle mass depletion. In a further embodiment, the method improves muscle mass recovery after illness or injury.

In an embodiment, the nutritional composition is used in a method of improving an individual's metabolism. The method includes administering to an individual who desires such improved metabolism an effective amount of the nutritional composition. In a further embodiment, the method enhances micro-nutrient absorption. In a further embodiment, the method improves bioavailability of micro-nutrients. In a further embodiment, the method provides greater caloric uptake. In a further embodiment, the method provides greater caloric uptake so that the individual is able to have a better morning start. In a further embodiment, the method provides a feeling of satiety. In a further embodiment, the method provides a feeling of satiety to avoid overeating. In a further embodiment, the method provides a feeling of satiety to decrease caloric intake. In a further embodiment, the method provides a feeling of satiety to treat obesity. In a further embodiment, the method provides sustained energy after such administering.

In an embodiment, the nutritional composition is used in a method for treating diabetes in a patient who can benefit from such treatment. The method includes administering to such patient an effective amount of the nutritional composition. In a further embodiment, the method decreases insulin resistance. In a further embodiment, the method decreases blood glucose excursions. In a further embodiment, the method decreases CVD risk.

An embodiment of the present disclosure includes a use of a polysaccharide, such as a gum in a nutritional composition that includes FOS and inulin for administration to an individual to provide nutrition thereto, wherein the polysaccharide is present in an amount effective to provide greater tolerance of such nutritional compositions when administered to the individual, with the polysaccharide, FOS and inulin being present in the amounts disclosed herein. In a further embodiment, the polysaccharide is AG.

An embodiment of the present disclosure includes a use of a polysaccharide, such as a gum for preparation of a nutritional composition for promoting gut microbiota balance and health in an individual, wherein the nutritional composition also includes a FOS and inulin, in the amounts disclosed herein. In a further embodiment, the polysaccharide is AG.

In an embodiment, the nutritional composition is used in a method of use of an effective amount of the nutritional composition for long-term administration.

In an embodiment, the nutritional composition is used in a method of use of an effective amount of the nutritional for short-term administration.

In an embodiment, the nutritional composition is used in a method of use of an effective amount of the nutritional composition for tube-feed administration.

In an embodiment, the nutritional composition is used in a method of modulating hormones produced by the gastrointestinal tract or regulated by the gastrointestinal tract comprising administering to an individual that can benefit from the same an effective amount of the nutritional composition. In a further embodiment, the inflammatory hormones are decreased in the individual. In a further embodiment, a feeling of well being of the individual is increased. In a further embodiment, the serotonin is increased. In a further embodiment, the serotonin leads to improved sleep patterns in the individual. In a further embodiment, the serotonin leads to improved sleep quality for the individual. In a further embodiment, the serotonin leads to a decrease in depression. In a further embodiment, the serotonin leads to a normalization of appetite. In a further embodiment, cognition is improved.

In an embodiment, the nutritional composition is used in a method for improving bacterial balance in a pediatric patient by administering to an individual who can benefit from the same an effective amount of the nutritional composition wherein there is decreased TH1/TH2 imbalance, TH1/TH2 imbalance is a favoring of the TH2 subset. In a further embodiment, the decreased TH1/TH2 imbalance leads to a decreased incidence of allergies. In a further embodiment, the decreased TH1/TH2 imbalance leads to a decreased incidence of atopic dermatitis. In a further embodiment, the decreased TH1/TH2 imbalance leads to a decreased incidence of asthma. In a further embodiment, the decreased TH1/TH2 imbalance leads to a decreased incidence of food allergies. In a further embodiment, the decreased TH1/TH2 imbalance leads to a decreased incidence of otitis media. In a further embodiment, the decreased TH1/TH2 imbalance leads to a decreased incidence of viral infections. In a further embodiment, the decreased TH1/TH2 imbalance leads to a decreased incidence of autoimmune diseases. In a further embodiment, the decreased TH1/TH2 imbalance leads to a decreased incidence of allergic rhinitis.

In an embodiment, the nutritional composition is used in a method for providing nutrition to a patient with a renal disorder. The method includes administering to such patient an effective amount of the nutritional composition. In a further embodiment, the patient is in renal failure. In a further embodiment, the patient undergoes dialysis treatments.

In an embodiment, the nutritional composition is used in a method for management of at least one inflammatory condition by administering to an individual patient an effective amount of the nutritional composition. In a further embodiment, the inflammatory condition is prevention of an inflammatory condition. In a further embodiment, the inflammatory condition is gastrointestinal inflammation. In a further embodiment, the inflammatory condition is inflammatory bowel disease ("IBD").

In an embodiment, the nutritional composition is used in a method that leads to a decrease in healthcare spending costs. In a further embodiment, the decrease in healthcare spending costs is due to decreased length of stay in a hospital. In a further embodiment, the decrease in healthcare spending costs is due to decreased length of stay in a care facility. In a further embodiment, the decrease in healthcare spending costs is due to decreased complications. In a further embodiment, the decrease in healthcare spending costs is due to decreased incidence of diarrhea. In a further embodiment, the decrease in healthcare spending costs is due to decreased incidence of constipation. In a further embodiment, the decrease in healthcare spending costs is due to decreased incidence of diverticulitis.

The foregoing description of various aspects of the present disclosure have been presented for purposes of illustration and description. It is not intended to be exhaustive or to limit the present disclosure to the precise form disclosed, and obviously, many modifications and variations are possible. Such modifications and variations that may be apparent to a person skilled in the art are intended to be included within the scope of the present disclosure as defined by the accompanying claims.

EXAMPLES

Example 1

Enteral Formula Containing Pro- and Prebiotics in Pediatric Intensive Care Unit (PICU): Tolerance, Safe Use and Intestinal Ecology Background This project was aimed at renovating a supplement with an innovative nutritional concept to increase the product's value proposition in the benefit area of growth and protection (reinforces child defenses).

For that purpose the formula was enriched with a blend of two probiotic bacteria *Lactobacillus paracasei* NCC2467 (ST11) and *Bifidobacterium longum* NCC 3001 (Bb536), a unique combination of PREBIO1™:AG and DHA.

For substantiation of the tolerance/safety and the benefit in the context of health care environment, a clinical trial was initiated:

Clinical Trial

The clinical trial was conducted in Nakhon Ratchasima, Thailand with 94 hospitalized children in pediatric intensive care unit ("PICU") in need of mechanic ventilation and enteral feeding. The study was performed during almost 3 years. The tolerance/safety analysis takes into consideration both overall percentage of caloric intake and time to achieve the target caloric intake while benefits analysis evaluates fecal microbiota composition, including presence of the strains NCC 2461 (ST11) and NCC 3001 (BB536).

Methods

This was a double blind, controlled, randomized clinical trial. Two products were under investigation, an experimental product and a control product.

Experimental Product (New Nutren Junior)

Enteral formula with probiotics NCC2461/NCC3001+prebiotics (PREBIO1™+AG)+DHA.

Control Product (Nutren Junior)

Isocaloric and isoprotein formula without added pro- and prebiotics or DHA.

Results 94 patients were randomized and intended to treat, all having had at least at one day some study product intake. 88 patients had more than 3 days of enteral feeding (PP data set).

Tolerance/Safety Analysis

Overall Percentage of Caloric Intake

Overall percentage of caloric intake during hospitalization was calculated by summing up total volume administered in 24 hours over available days divided by number of days times weight times 70 kcal/kg/day. This was done for each subject. Overall percentage of caloric intake was analyzed by Wilcoxon rank-sum test, confidence intervals were calculated according to Hodges-Lehman. Summary statistics and the treatment difference are presented in Table 2.

TABLE 2

Summary statistics on overall percentage of caloric intake and the treatment difference. For summary statistics median and quartiles are presented, for the treatment difference the pseudo median and the two-sided 95% confidence interval. All refers to the PP data set.

| data set | New Nutren Junior | | | Nutren Junior | | | 95% CI | | |
|---|---|---|---|---|---|---|---|---|---|
| | median | 25% | 75% | median | 25% | 75% | Δ | lower | upper |
| PP | 76.2 | 65.3 | 84.3 | 75.1 | 69.2 | 83.6 | 0.3 | −7.1 | 7.9 |

The two-sided 95% confidence interval goes from −7.1% to 7.9% overall caloric intake. The lower boundary of the confidence interval, −7.1% is greater than −15% that was defined as significant difference. Thus, non inferiority between the two products was demonstrated.

Time to Achieve the Target Caloric Intake

Time to achieve the targeted daily caloric intake is time when daily energy intake ("DEI") passes 100%. As it was not expected that a child would reach exactly 100% at a certain day, this time was calculated for each child by linear interpolation between the day before 100% and the day after 100% DEI was measured. Children who did not reach the daily caloric goal during the 7 days of tube feeding were censored. As shown in the Kaplan Meier plot presented in FIG. 1, 36% and 29% of the children did not reach the caloric goal in the test and control groups, respectively, over 7 days. The median time to achieve the caloric goal was 5.10 and 5.03 days in the test and control groups, respectively. The time difference was 1 hour, the 95% confidence interval goes from 29 hours to 61 hours. This further shows the non-inferiority between the two tested products.

Time to achieve the caloric goal was also analyzed by a log-rank test. The p-value is 0.67. Median time to achieve the goal is presented by treatment group in Table 3.

TABLE 3

Summary statistics on time to achieve the caloric goal. Median time and the two-sided 95% confidence interval are presented. All refers to the PP data set.

|  | n | events | median | 95% CI lower | 95% CI upper |
|---|---|---|---|---|---|
| New Nutren Junior | 44 | 28 | 5.10 | 4.64 | ∞ |
| Nutren Junior | 44 | 30 | 5.03 | 4.46 | 6.14 |

Safety was addressed through general improvement of health status and parameters of tolerance as supportive evidences (abdominal distension, vomiting, stool frequency/diarrhea, etc.). Use of enteral formula containing pre- and probiotics was found to be safe in respect to the 4 parameters indicated above.

According to clinical records the patients from both groups recovered from critical condition and were finally discharged from the PICU in the time frame of regular clinical practices (max. +/−7 days post-hospitalization). Moreover, no product-related side effects were reported by the investigator during the study, supporting the safety of the tested products.

Prebiotic Benefits Analysis

Fecal microbiota composition was selected as a key parameter reflecting the gut balance in such critical environment (patients under antibiotic treatment with high risk of infections). The following bacterial groups were measured: the genus *Bifidobacterum*, the genus *Lactobacillus*, the group *Bacteroides/Porphyromonas/Prevotella*, the family Enterobactericeae, the species *Clostridium perfringens* and the genus *Enterococcus*. Mean values (log 10) are presented in the Table 4.

TABLE 4

Summary statistics on bacteria families (log10 scale), PP data set.

|  |  | Nutren Junior | | | | | | New Nutren Junior | | | | | |
|---|---|---|---|---|---|---|---|---|---|---|---|---|---|
|  |  | n | n > DL | p > DL | min | mean | max | n | n > DL | p > DL | min | mean | max |
| Bifidobacteria | Baseline | 40 | 32 | 80% | 5.00 | 7.72 | 9.95 | 43 | 35 | 81% | 3.00 | 7.01 | 10.11 |
|  | 7 days | 39 | 28 | 71% | 3.00 | 7.03 | 10.00 | 41 | 27 | 65% | 3.00 | 7.36 | 9.60 |
|  | 14 days | 36 | 25 | 69% | 5.00 | 7.20 | 9.52 | 37 | 30 | 81% | 5.00 | 7.76 | 9.78 |
| Lactobacilli | Baseline | 40 | 38 | 95% | 3.48 | 5.84 | 9.40 | 44 | 42 | 95% | 3.00 | 5.56 | 8.48 |
|  | 7 days | 39 | 38 | 97% | 3.30 | 6.03 | 9.27 | 42 | 40 | 95% | 3.48 | 5.86 | 9.95 |
|  | 14 days | 36 | 35 | 97% | 3.00 | 5.81 | 9.16 | 38 | 38 | 94% | 4.11 | 6.56 | 8.85 |
| *Bacteroides* | Baseline | 40 | 37 | 92% | 6.20 | 8.75 | 10.43 | 44 | 42 | 95% | 5.00 | 8.57 | 10.28 |
|  | 7 days | 39 | 38 | 97% | 5.00 | 8.56 | 10.30 | 42 | 39 | 92% | 5.60 | 8.62 | 10.36 |
|  | 14 days | 36 | 34 | 94% | 5.00 | 8.47 | 10.23 | 38 | 35 | 92% | 5.00 | 8.66 | 10.11 |
| Enterobacteria | Baseline | 40 | 38 | 95% | 3.48 | 7.92 | 9.70 | 44 | 40 | 90% | 3.30 | 7.57 | 9.30 |
|  | 7 days | 39 | 36 | 92% | 4.45 | 7.62 | 9.48 | 42 | 39 | 92% | 3.00 | 6.61 | 9.95 |
|  | 14 days | 36 | 34 | 94% | 3.00 | 7.46 | 8.85 | 38 | 38 | 100% | 3.00 | 7.08 | 9.30 |
| *Clostridium perfringens* | Baseline | 40 | 13 | 32% | 3.48 | 5.50 | 7.60 | 44 | 14 | 31% | 3.00 | 4.58 | 5.95 |
|  | 7 days | 39 | 7 | 17% | 3.48 | 4.69 | 7.85 | 42 | 4 | 9% | 3.48 | 3.73 | 3.95 |
|  | 14 days | 36 | 11 | 30% | 3.00 | 4.57 | 7.48 | 38 | 11 | 28% | 3.00 | 4.47 | 6.15 |
| Enterococci | Baseline | 40 | 37 | 92% | 3.70 | 6.72 | 9.29 | 44 | 41 | 93% | 3.00 | 6.25 | 9.23 |
|  | 7 days | 39 | 34 | 87% | 3.48 | 7.49 | 9.45 | 42 | 38 | 90% | 3.00 | 7.08 | 9.67 |
|  | 14 days | 36 | 32 | 86% | 4.43 | 7.30 | 9.33 | 38 | 36 | 94% | 3.00 | 7.22 | 9.82 |

Where n is number of subjects, n > DL number of subjects with measurements above the detection limit, p > DL percentage of subjects with measurements above the detection limit.

Within the genus *Bifidobacterium*, the strain *Bifidobacterium longum* NCC 3001 was identified by specific PCR and within the genus *Lactobacilli*, the strain *Lactobacillus paracasei* NCC 2461 was also identified by specific PCR. The NCC 3001 and NCC 2461 strains were identified in 18% 84% of the patients receiving enteral formula with pre- and probiotics during the PICU stay.

The differences in change scores from baseline of *Bifidobacteria*, between the control and test group was 0.17 log 10 CFU/mg and 1.43 log 10 CFU/mg at 7 days and 14 days, respectively. The difference at 14 days was statistically significant, p=0.013. The increase in *Bifidobacteria* should not be solely attributed to the *Bifidobacterium* strain contained in the test product but might also reflects an additional bifidogenic effect of the prebiotic blend (PREBIO1™+AG) added in the product. Differences for *lactobacilli* follow the same trend (not significant) with a level 0.75 log higher in the test group compared to control at end of supplementation period (day 14). Mean values of Bacteroides and Enterococci levels were maintained unchanged in both treatment groups.

There was, in both groups, a progressive decline in *Clostridium perfringens* levels along the hospitalization period (PICU). Same observation was made for Enterobacteria. Although not statistically significant, the effect for the latter was more pronounced (approx. 1 log decline at 7 days) upon feeding with test product.

Conclusions

The results show that enteral feeding with the a supplement comprising both PREBIO1™ and AG is better tolerated than the Nutren Jr. already on the market comprising only PREBIO1™. Moreover, in comparison to Nutren Jr., the New Nutren Jr. is more effective in promoting not only the reduction of bacterial groups comprising known pathogens among their members (Enterobacteria, *Clostridia*), but also the increase of microbial groups of reputed beneficial effects (*Bifidobacteria*), thus positively balancing the microbiota composition in sick children.

Example 2

Enteral Formula Containing Pro- and Prebiotics in PICU: Tolerance, Safe Use and Intestinal Ecology Background Malnutrition in hospitalized infants together with global disturbances of the intestinal microbiota are conditions that favor both acute episodes of diarrhea as well as the long term harboring of intestinal pathogens source of nosocomial infections.

Objectives

The present study aimed to demonstrate the tolerance of an enteral formula containing pro- and prebiotics, its safe use in the PICU and its capacity to support intestinal bacterial ecology.

Design/Methods

94 PICU patients between 1-3 years of age in need of mechanical ventilation and enteral feeding were randomized to receive a test formula containing probiotics, prebiotics and DHA or a control isocaloric and isoprotein formula. Patients remained 7 days in the PICU and were further examined at day 14. The primary objective was to evaluate tolerance measured by progression to caloric target and secondary objectives were to determine the safe use and the improvement of gut microbiota.

Results

Overall caloric intake was not different between the two formulations. The median time to reach caloric goal was 5.1 in the test group and 5.03 in the control group (p=0.67).

Regarding safety, patients from both groups recovered from critical condition and were discharged from PICU within the time frame of the current clinical practice. As supportive evidence for the safe use of enteral formulas no difference in abdominal distension, vomiting and stool frequency/diarrhoea were observed between the two tested products. Moreover, no side effects were observed in either of the groups.

*Bifidobacteria* diminished in the control group whereas they augmented in the test group reaching a statistical significance difference at day 14 (P=0.013). A similar trend was observed for *Lactobacilli* with levels 0.75 log higher in the test group vs. control (NS). The probiotic *Lactobacillus paracasei* NCC2461 strain used in the study was recovered from feces in 84% of the cases. *Bifidobacterium longum* NCC3001 strain the second probiotic strain was recovered in only 18% of cases. Bacteroides and Enterococci remained unchanged. A progressive decline in *Clostridium perfringens* during hospitalization was observed in both groups. While Enterobacteria levels remained unchanged in the control group their levels diminished by 1 log in the test group during the PICU stay.

Conclusions

The use of pro- and prebiotic supplemented formula does not change the tolerance of enteral nutrition in the PICU. Moreover, such formula is safe and promotes a positive balance of the microbiota composition in critically ill children.

Example 3

In Vitro Evaluation of a Prebiotic Blend Using the Simulator of the Human Intestinal Microbial Ecosystem ("SHIME")

In vitro evaluation of two prebiotic blends have been performed in which a simulator of the human gastrointestinal tract (TWINSHIME model) was used to evaluate the prebiotic activity of a prebiotic blend of the present nutritional compositions (referred to as "Blend$^{1+}$") for application as either an oral nutritional supplement ("ONS") or in a tube-feeding formulation ("TF"). The focus of the evaluation was to assess the impact of partial substitution of FOS and inulin by AG in an original fiber blend (referred to as "Blend$^{1}$") on microbial fermentation characteristics in an ONS strategy.

In vitro approaches to study the gastrointestinal tract and intestinal microbial processes offer an excellent experimental setup to study possible prebiotic properties of selected food ingredients. The application of well-designed continuous models allows the in-depth study of the biological activity of selected molecules in the gut under representative environmental conditions. Furthermore, recent advances in in vitro modeling also allow to combine the study of bacteria-host interactions, such as mucosal adhesion and interaction with the immune system, with the continuous model, thereby further increasing both the scientific output and commercial relevance.

The two prebiotic blends that were used in this study included 30% fat, 20% proteins and 50% carbohydrates. The blends differed in carbohydrate composition. Blend$^{1}$ ("SHIME1") contained FOS and inulin in a 70% to 30% ratio. Blend$^{1+}$ ("SHIME2") contained 41% FOS, 41% acacia gum, 18% inulin. The products were available in servings containing 3.3 g of fibers. A total amount corresponding to two servings of the blends per day was administered to the respective SHIME model. The blends were administered to the models as part of the liquid nutritional medium which enters the stomach compartments three times per day, resulting in the administration of 3 times 2.2 g fiber per day.

Simulator of the Human Intestinal Microbial Ecosystem

To study potential prebiotic properties of the selected products in detail using an in vitro setup, a continuous model was used, which allows to culture the complex intestinal microbial ecosystem over a long period and under representative conditions. Moreover, as previous in vitro and in vivo studies have shown that the evaluation of prebiotic properties may only be performed after two to three weeks of continuous administration of the compound, the model should allow to simulate repeated ingestion of the prebiotic. Therefore, the dynamic SHIME simulator of the human gastrointestinal tract was used to evaluate the efficacy of the prebiotic treatment.

Figure 2:
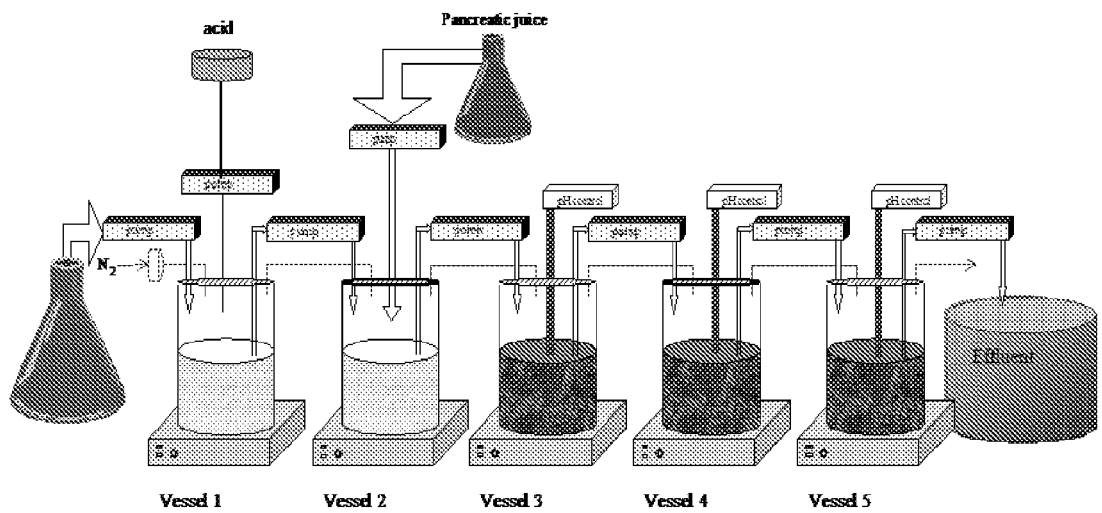
FIG. 2 shows a standard setup of a Simulator of the Human Intestinal Microbial Ecosystem ("SHIME"), which includes five sequential reactors that simulate the different regions of the human intestinal tract.
Figure 3A:
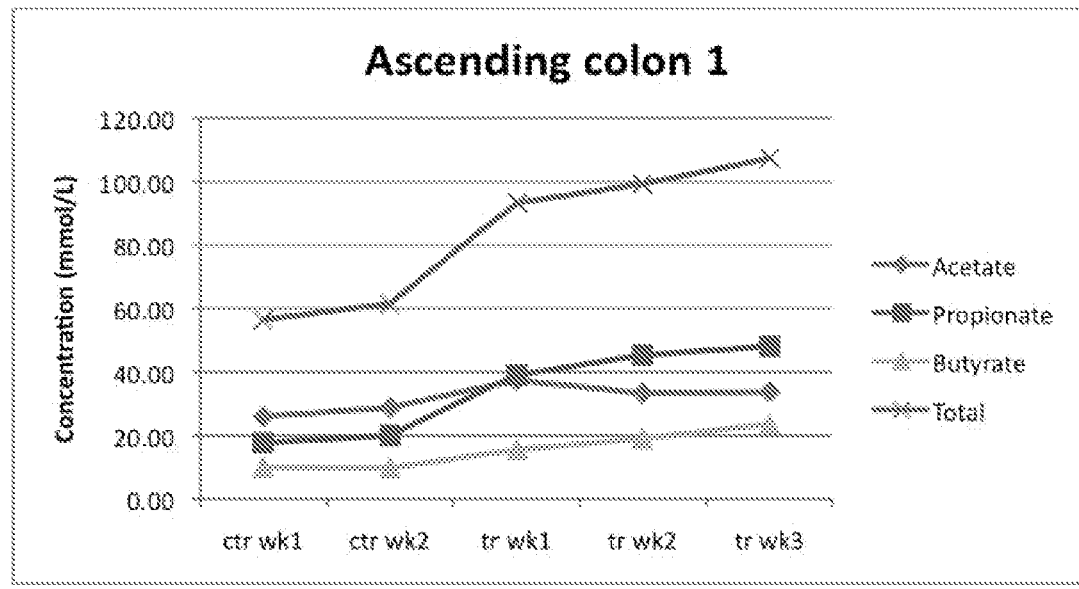
FIGS. 3A-3F show graphs of concentrations of total SCFA, acetate, propionate and butyrate in the ascending, transverse and descending colon for experiments performed with Blend[1] (designated by the number "1") and Blend[1+] (designated by the number "2").
Figure 3B:
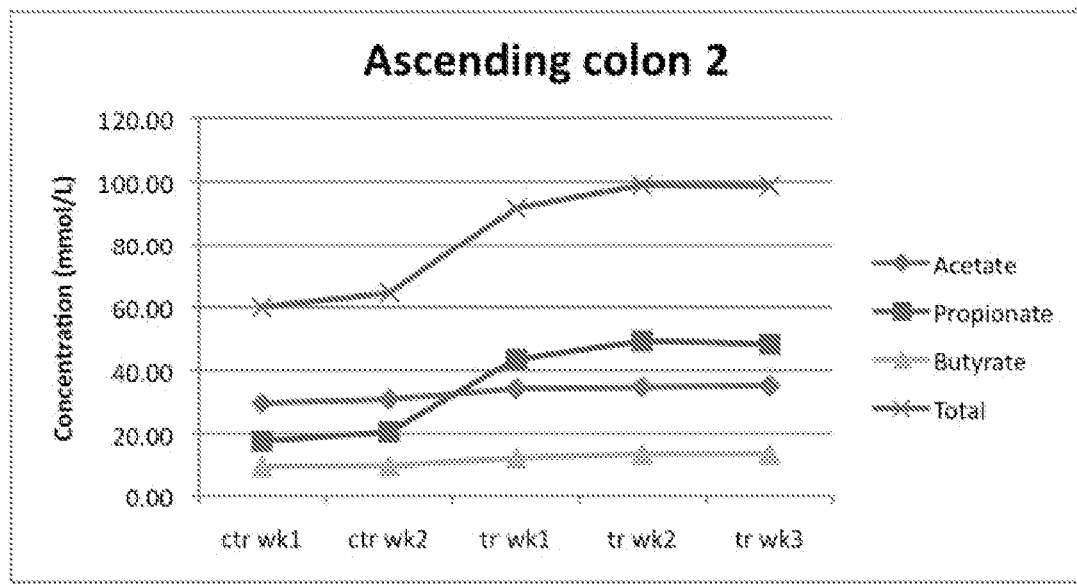
Figure 3C:
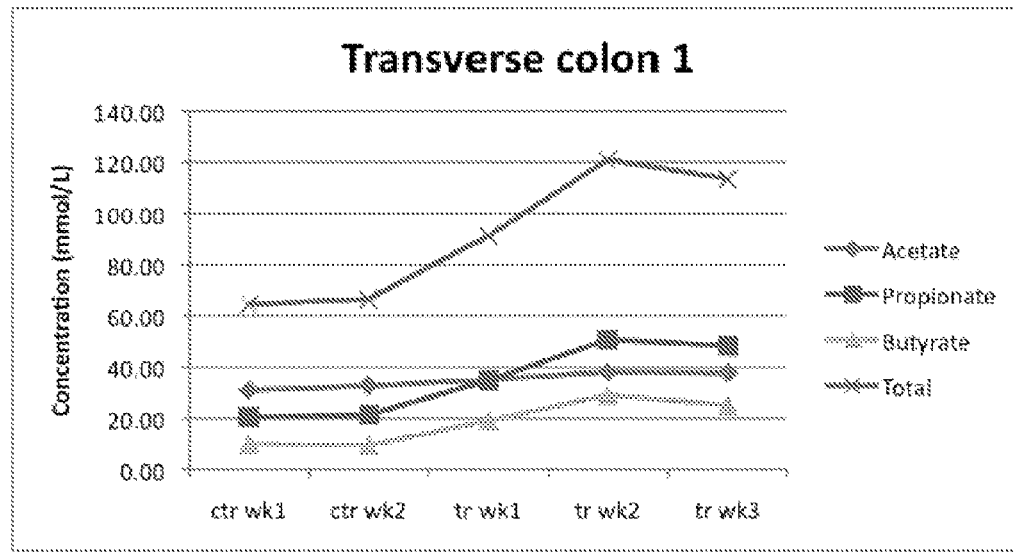
Figure 3D:
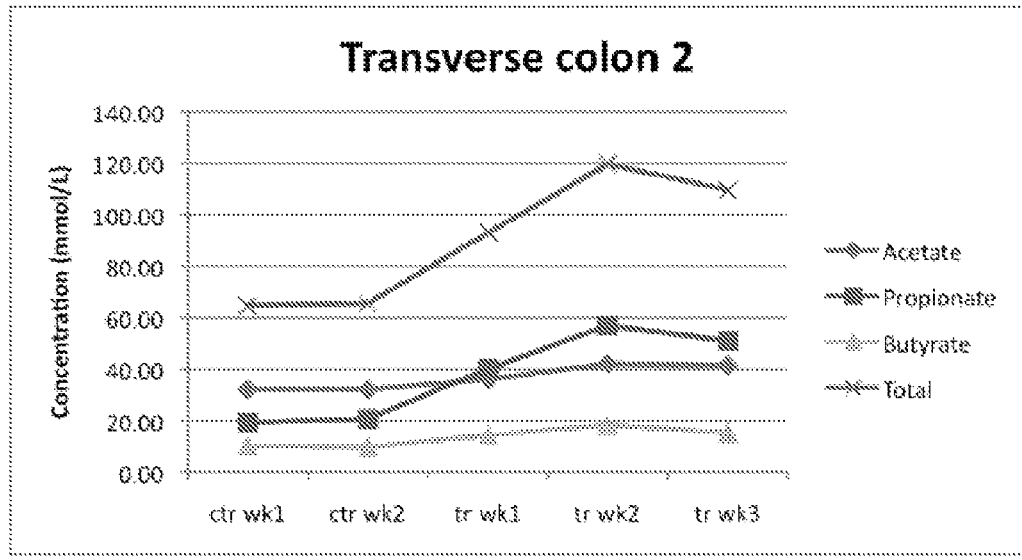
Figure 3E:
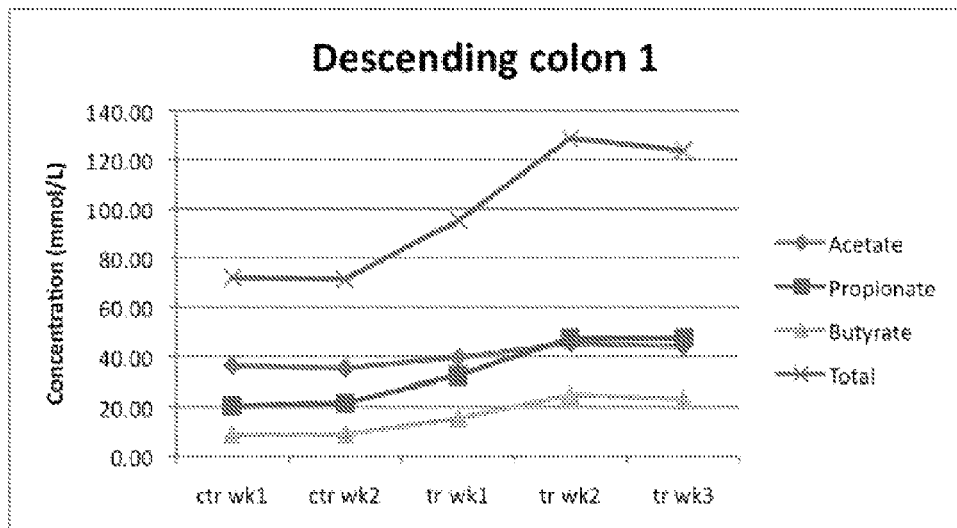
Figure 3F:
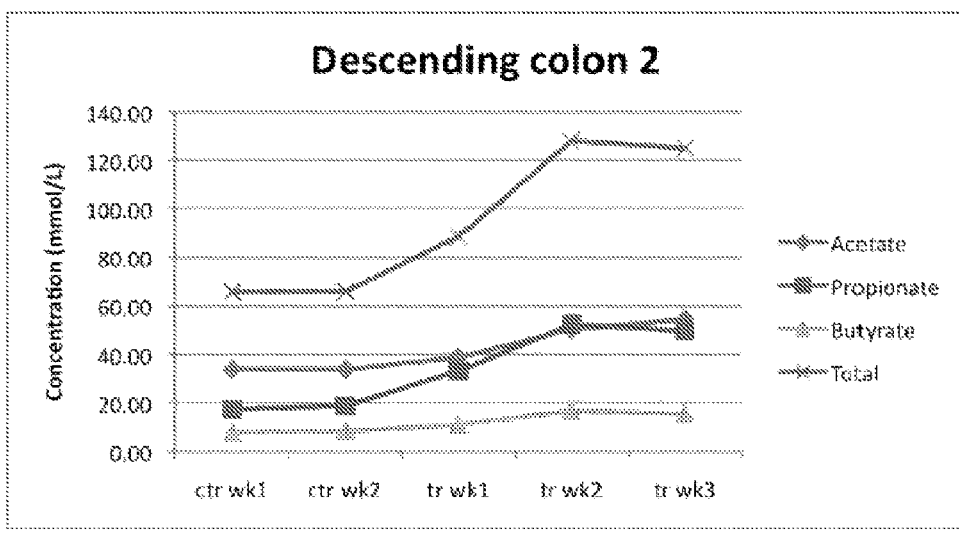
Figure 4A:
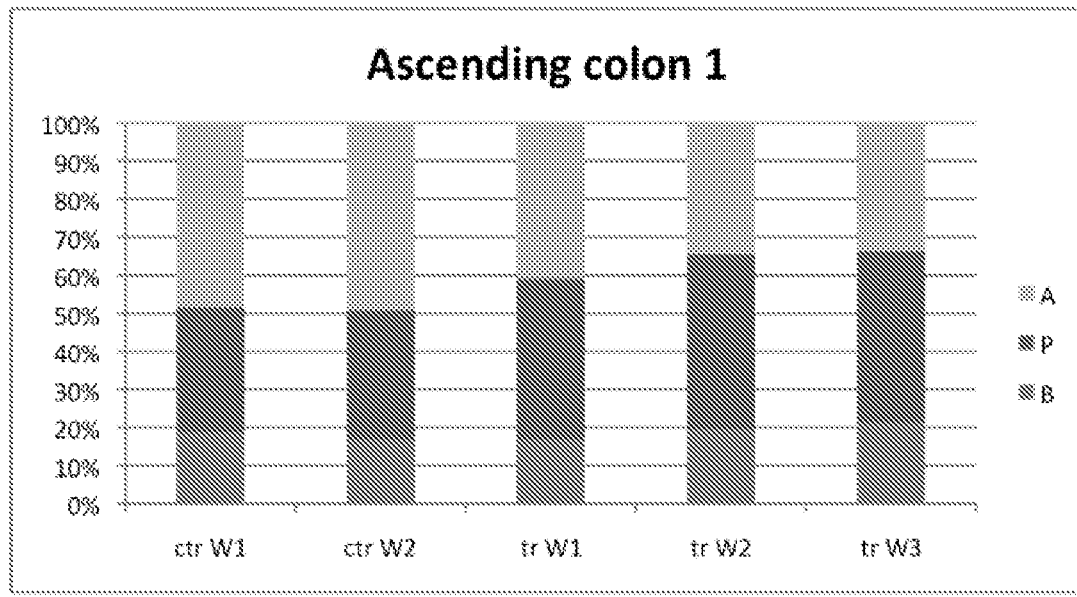
FIGS. 4A-4F show bar charts of A/P/B ratios in the ascending, transverse and descending colon from experiments run with Blend[1] (designated by the number "1") and Blend[1+] (designated by the number "2").
Figure 4B:
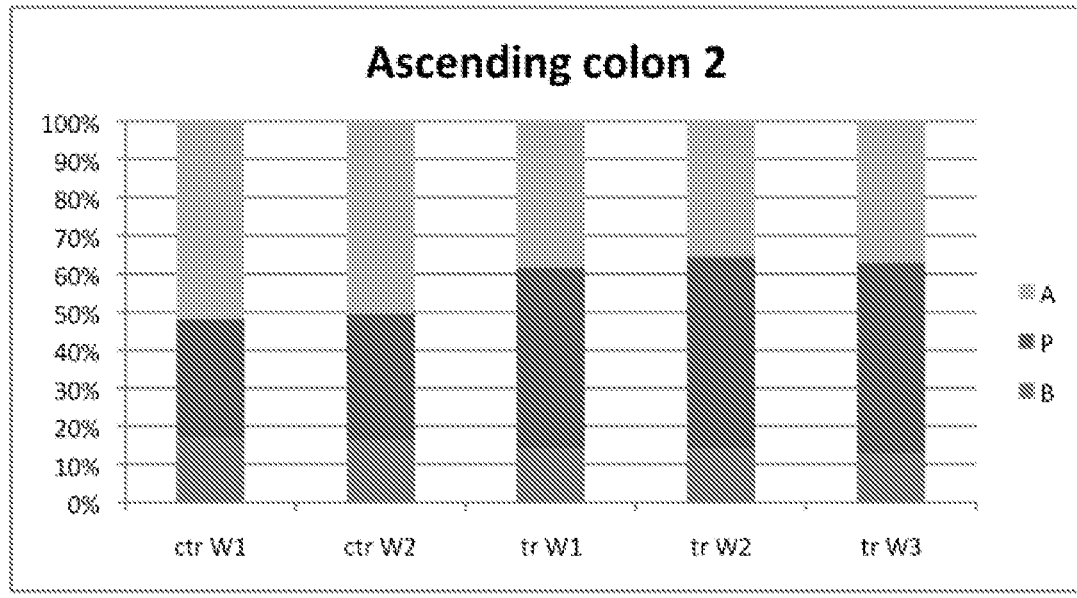
Figure 4C:
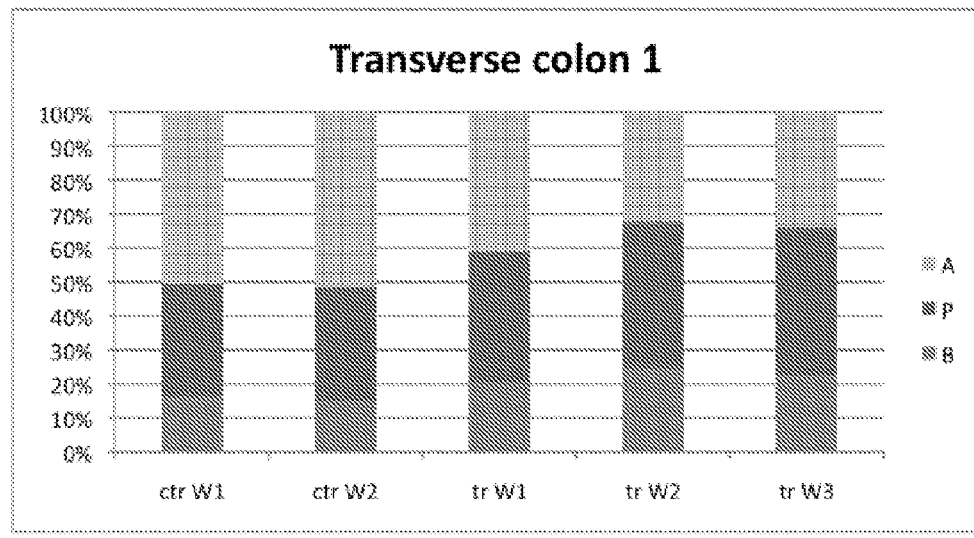
Figure 4D:
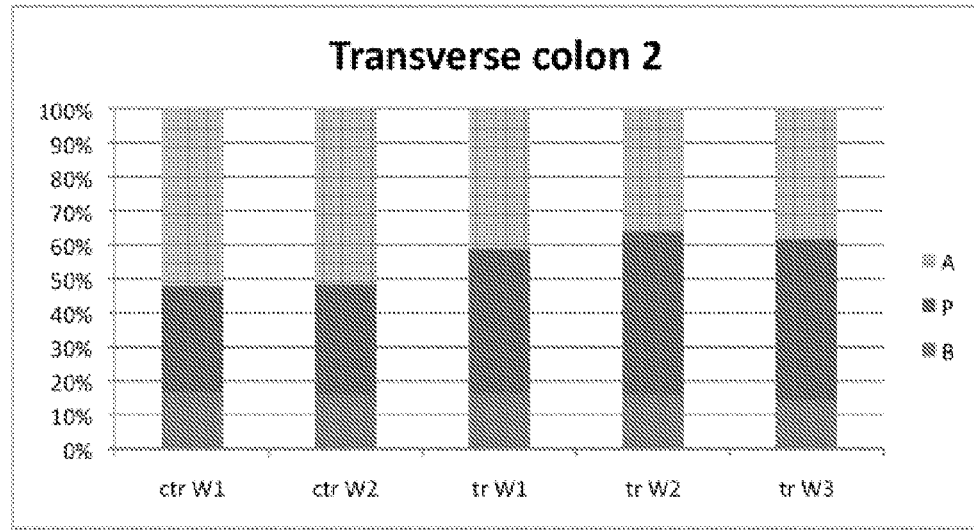
Figure 4E:
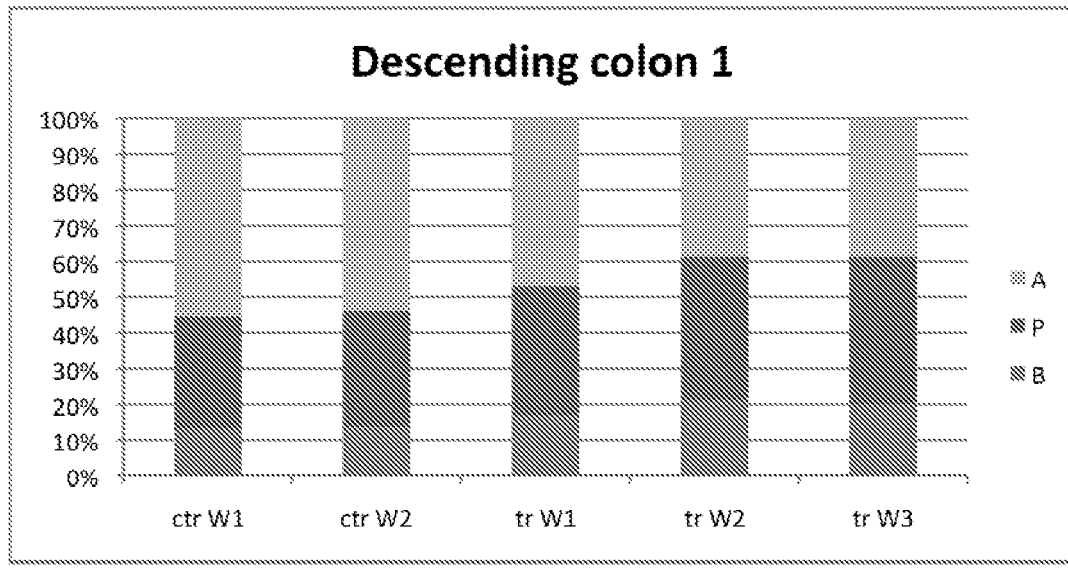
Figure 4F:
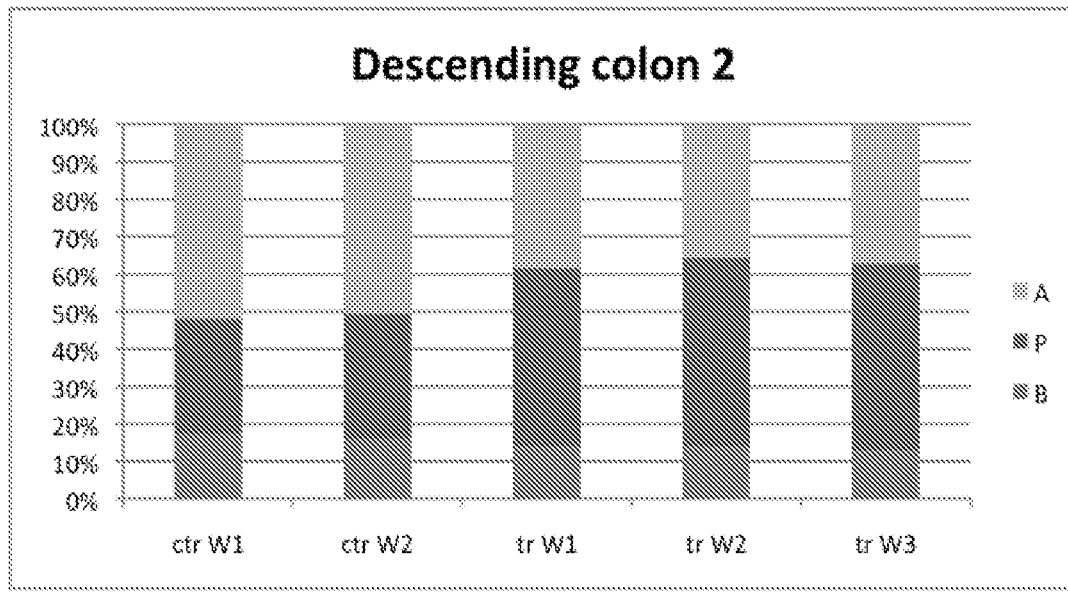

The reactor setup was adapted from the SHIME, representing the gastrointestinal tract ("GIT") of the adult human, as described by Molly et al. See, Molly, et al., "Development of a 5-step multichamber reactor as a simulation of the human intestinal microbial ecosystem," *Applied Microbiology and Biotechnology* 39: 254-258 (1993). The SHIME consists of a succession of five reactors simulating the different parts of the human gastrointestinal tract. See, e.g., FIG. 2.

The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach (V1) and duodenum (V2) compartment and emptying the respective reactors after specified intervals. The last three compartments are continuously stirred reactors with constant volume and pH control. Retention time and pH of the different vessels are chosen in order to resemble in vivo conditions in the different parts of the gastrointestinal tract. The overall residence time of the last three vessels, simulating the large intestine, is 72 hours. Upon inoculation with fecal microbiota, these reactors simulate the ascending (V3), transverse (V4) and descending (V5) colon. Inoculum preparation, retention time, pH, temperature settings and reactor feed composition were previously described by Possemiers et al. See, Possemiers et al., "PCR-DGGE-based quantification of stability of the microbial community in a simulator of the human intestinal microbial ecosystem," *FAMS Microbiology Ecology* 49: 495-507 (2004).

The SHIME has been extensively used for more than 15 years for both scientific and industrial projects and has been validated with in vivo parameters. Upon stabilization of the microbial community in the different regions of the colon, a representative microbial community is established in the three colon compartments, which differs both in composition and functionally in the different colon regions.

For these experiments, a TWINSHIME setup was used by operating two systems in parallel at the same time (SHIME1=Blend$^1$; SHIME2=Blend$^{1+}$). Identical environmental conditions for both systems were obtained by identical pH and temperature control and by using two-headed pumps for liquid transfer between the reactors.

The SHIME experiment consisted of 3 stages. The first stage was a start-up stage. After inoculation of the colon reactors with an appropriate fecal sample (elder donor with a low concentration of *bifidobacteria*), a two-week start up period allowed the microbial community to differentiate in the different reactors depending on the local environmental conditions. The second stage was a control period that was the actual start of the experiment, in which standard SHIME feed was dosed to the model for a period of 14 days. The basal medium was composed as follows: arabinogalactan (1 g/L), pectin (2 g/L), xylan (1 g/L), starch (3 g/L), glucose (0.4 g/L), yeast extract (3 g/L), peptone (1 g/L), mucin (4 g/L), cysteine (0.5 g/L). Analysis of samples in this period allowed to determine the baseline microbial community composition and activity in the different reactors, which have been used as control to compare with the results from the prebiotic treatment. The third and final stage was a treatment period. During this three week period the SHIME reactor was operated under nominal conditions, but with a modified diet containing a lower amount of starch in the medium compared to that of the basal period (1 g/L). This allowed to pinpoint the effect of the two products on the top of a diet typical in elderly (diet containing low nutrients). In parallel, the diet of the SHIME was supplemented with the prebiotic (corresponding to two servings of the blends per day).

Results

A number of microbial parameters have monitored throughout the entire experiment including, for example, short-chain fatty acids, ammonium, lactate analysis, gas analysis, intestinal pH and sample collection.

Short-Chain Fatty Acids ("SCFA's")

SCFA are the typical end products of mainly saccharolytic fermentation by the intestinal bacteria and SCFA profiles consist mainly of acetate, propionate and butyrate with small amounts of other acids such as isobutyric, valeric, isovaleric and caproic acid. Whereas acetate can be absorbed from the gut and used as energy substrate by the host, butyrate acts as main energy substrate for the gut epithelium and has proven protective effects against inflammation and colon cancer. Propionate finally, has similar local activity in the gut as compared to butyrate, yet is also transported to the liver where it was shown to have positive cholesterol-lowering effects and effects on glycemic control. For this reason, butyrate and propionate are considered more health-beneficial for the host as compared to acetate and modulation of the microbial fermentation profiles in the gut towards increased butyrate and/or propionate production is considered beneficial.

With respect to SCFA's, samples were collected 3×/week from all colon compartments to analyze the concentration of acetic acid, propionic acid, isobutyric acid, butyric acid, isovaleric acid, valeric acid, isocaproic acid and caproic acid. In FIGS. 3A-F, the data are presented as total SCFA, acetate, propionate and butyrate production per experiment week of the TWINSHIME experiment. As mentioned above, prebiotic properties are evaluated by a relative increase of propionate and/or butyrate in the total SCFA production. The data are also summarized per experimental period and per colon compartment in Tables 5 and 6.

As acetate ("A"), propionate ("P") and butyrate ("B") are the major SCFA produced by intestinal bacteria, the data may also be expressed as an A/P/B ratio. To do this, the production of each fatty acid is presented as the ratio of the concentration of each individual fatty acid to the sum of the concentrations of the three fatty acids. In this experiment, prebiotic effects of a treatment, as determined by a relative increase of propionate and/or butyrate production, were evaluated by an increase of P and/or B and a decrease of A in the A/P/B ratio. The A/P/B ratios are presented, per experiment week, in FIGS. 4A-F.

Based on the considerations made above, both products gave clear indications of prebiotic activity. Both treatments induced an increase in the total SCFA concentration in all the colon vessels, which indicates that both products are well fermented in the GIT. Moreover, both products induced a higher concentration of propionate and butyrate and were able to move the ratio Acetate-Butyrate-Propionate towards a healthier composition. When evaluating statistical differences in SCFA production between control and treatment, clear changes typically only start from the second week of treatment. This was also observed in this experiment and relates to the adaptation period the bacteria need to adapt to the new nutritional environment. This leads to gradual changes in the SCFA profiles during the first week of treatment (high standard deviation) and results often in a lack of statistical significance when comparing the average of the SCFA concentrations of the first treatment week with those of the control period. Upon adaptation to the fiber blends (starting from week 2 of the treatment period), clear significant differences were observed in SCFA profiles.

In FIGS. 5A-E, a comparison between the two SHIME systems is presented, allowing to compare the prebiotic potential of the original and adapted fiber blend. The comparison was performed separately for each week of the experiment. Within each week, the concentrations of total SCFA, acetate, propionate and butyrate in each colon compartment were compared by means one-way ANOVA, and individual means were compared using the Tukey's test.

Based on the two SHIME runs, it was found that no statistical differences in SCFA production were observed in any of the colon compartments during the control period ("ctr") indicating that the starting point for the two different treatments was similar. It was also found that no statistically significant differences were noted on the effect of the two products during the first week of the treatment period ("tr"). This is believed to be related to the adaptation period for the gut microbiota to adapt their metabolism to the administered test compounds. Further, starting from the second week of treatment statistical differences occurred. This indicates that both products had a distinct fermentation profile resulting in specific SCFA production profiles.

The instant experiment also demonstrates that partial replacement of FOS and inulin by acacia gum induced differences in bacterial fermentation profiles. First, the butyrogenic effect of Blend$^1$ was higher than Blend while Blend$^{1+}$ showed a higher propionate concentration (even if not always supported by statistics). Second, these findings show that although both blends had a very positive effect in terms of SCFA production, the specific fermentation profile depended on the specific composition of the blends.

Ammonium

Figure 6A:
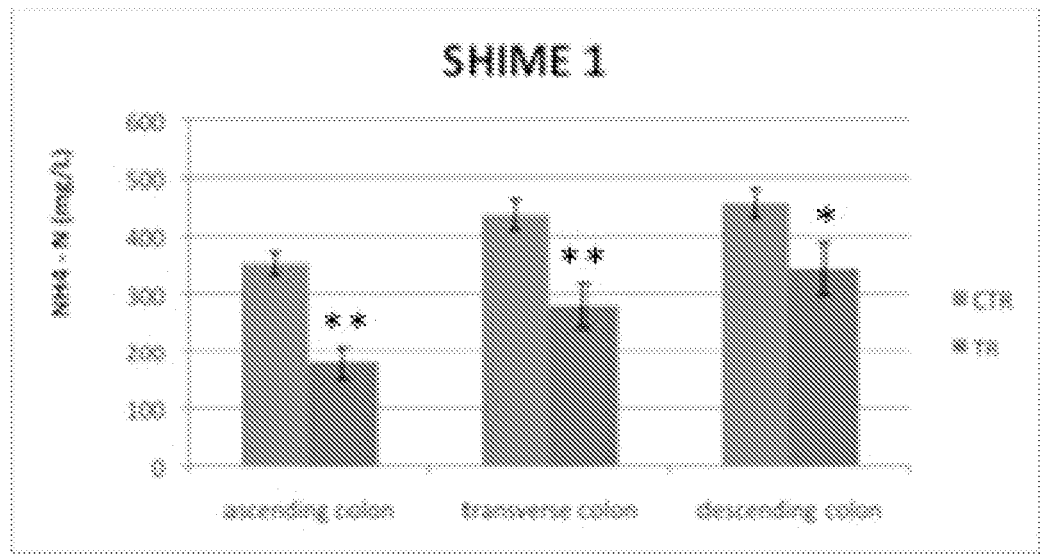
FIGS. 6A-6B show bar charts graphing ammonium concentrations (mg $NH_4^+/L$) in the ascending, transverse and descending colon for experiments performed using Blend[1] (designated as "SHIME 1") and Blend[1+] (designated as "SHIME 2"). The data is presented per experiment period. Significant differences in ammonium production (CTRL v. TREAT) have been assessed by means of a Student's two-tailed Ttest and are indicated with * for $P<0.05$ and ** for $P<0.01$.
Figure 6B:
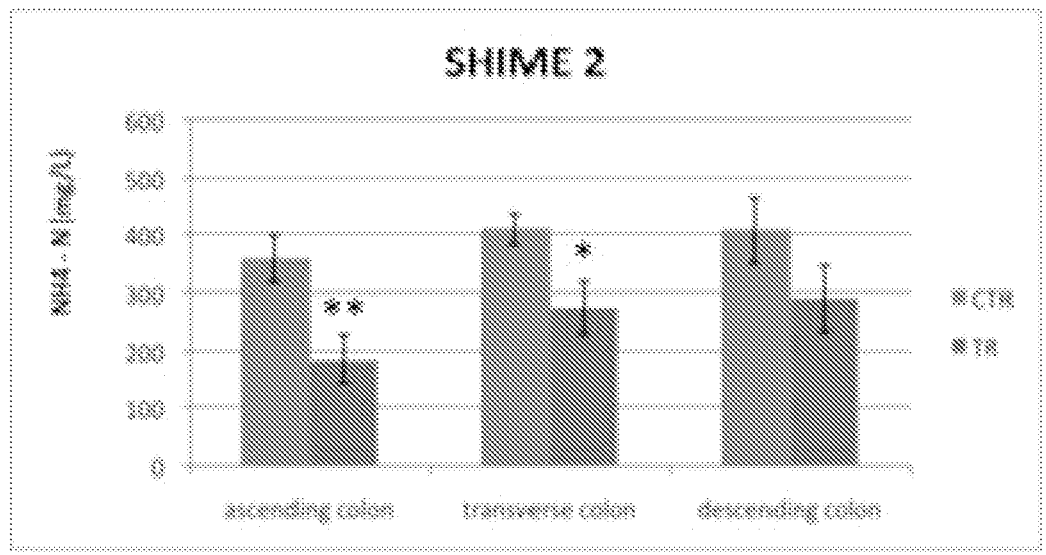

As ammonium production is mainly the result of protein degradation and is associated with direct and indirect health detrimental effects, a reduction in ammonium production would therefore be considered as beneficial. During this experiment, samples were collected 3 time per week from all colon compartments. The analysis of ammonium concentrations in the different colon regions throughout the course of the experiment is presented in FIGS. 6A and 6B. As is clearly indicated, both products induced a decrease in ammonium production during the treatment period.

Additionally, ammonium concentrations in the SHIME may also be seen as a marker for limited substrate availability for the bacteria during the treatment period. If certain bacteria cannot use the administered products as efficiently as they can utilize starch as energy source, these bacteria may shift to a more proteolytic metabolism, resulting in increased ammonium concentrations. The observed decrease in ammonium concentrations is, therefore, also a sign of a high fermentability of both blends.

Finally, no statistical differences were observed between the two SHIME runs, indicating that partial replacement of FOS and inulin by acacia gum did not affect the decrease in ammonium production, and that Blend$^{1+}$ was also well fermented, resulting in increased saccharolytic fermentation in the colon.

Lactate Analysis

Figure 7A:
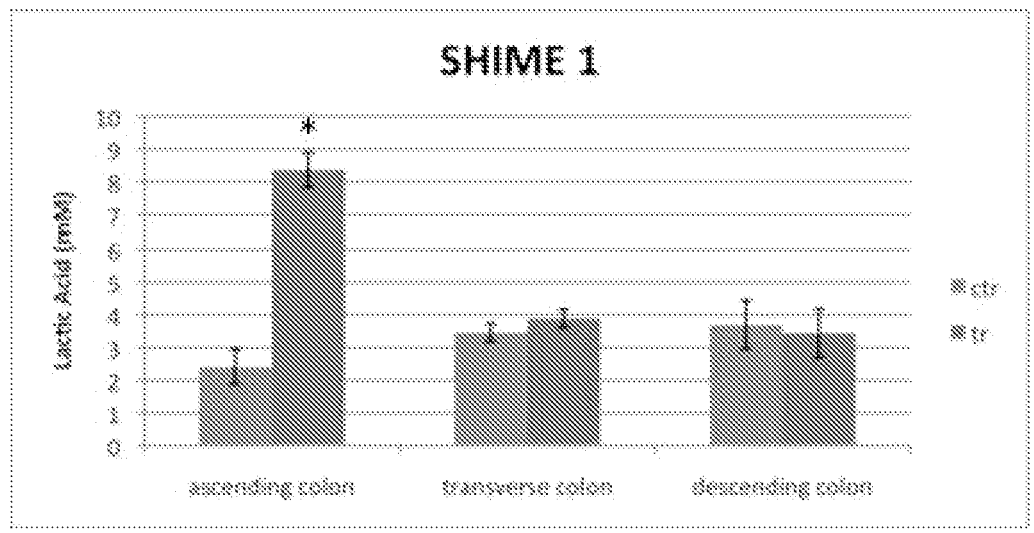
FIGS. 7A-7B show bar charts graphing lactate concentrations in the ascending, transverse and descending colon for experiments performed using Blend[1] (designated as "SHIME 1") and Blend[1+] (designated as "SHIME 2"). The data is presented per experiment period. Significant differences in lactate production (CTRL v. TREAT) have been assessed by means of a Student's two-tailed Ttest and are indicated with * for $P<0.05$.
Figure 7B:
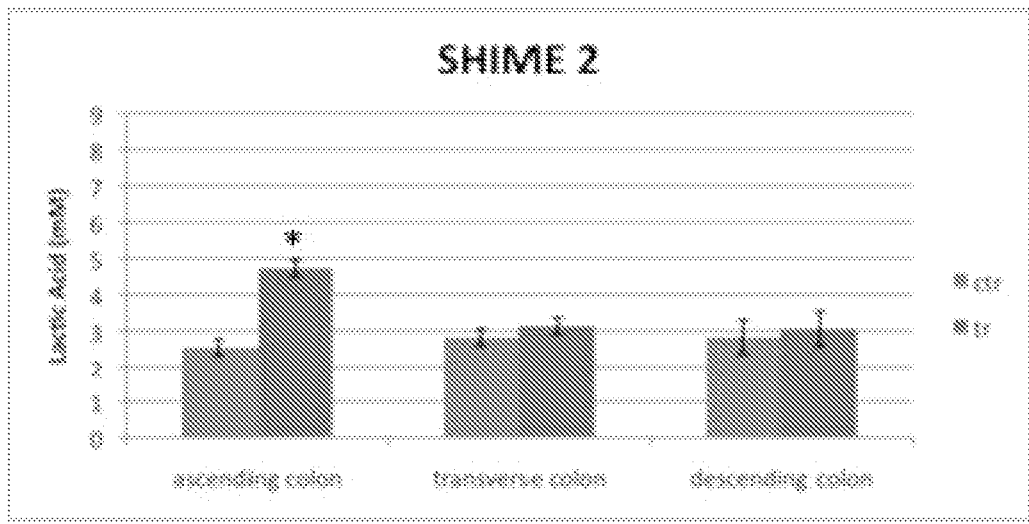
Figure 8A:
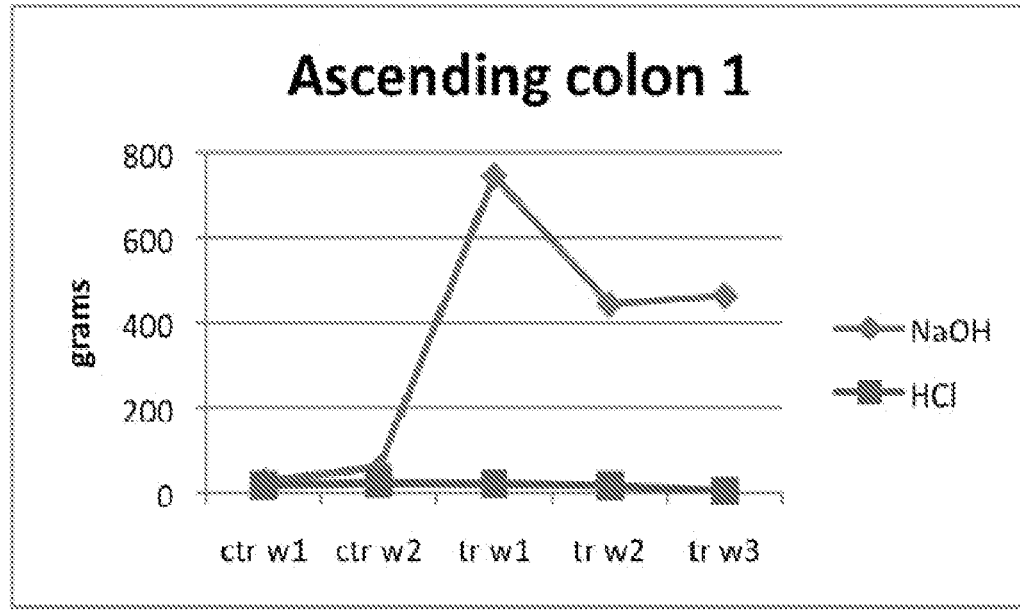
FIGS. 8A-8F show acid-base consumption in the ascending, transverse and descending colon for experiments performed using Blend[1] (designated as "SHIME 1") and Blend[1+] (designated as "SHIME 2"). The data is presented per experiment period.
Figure 8B:
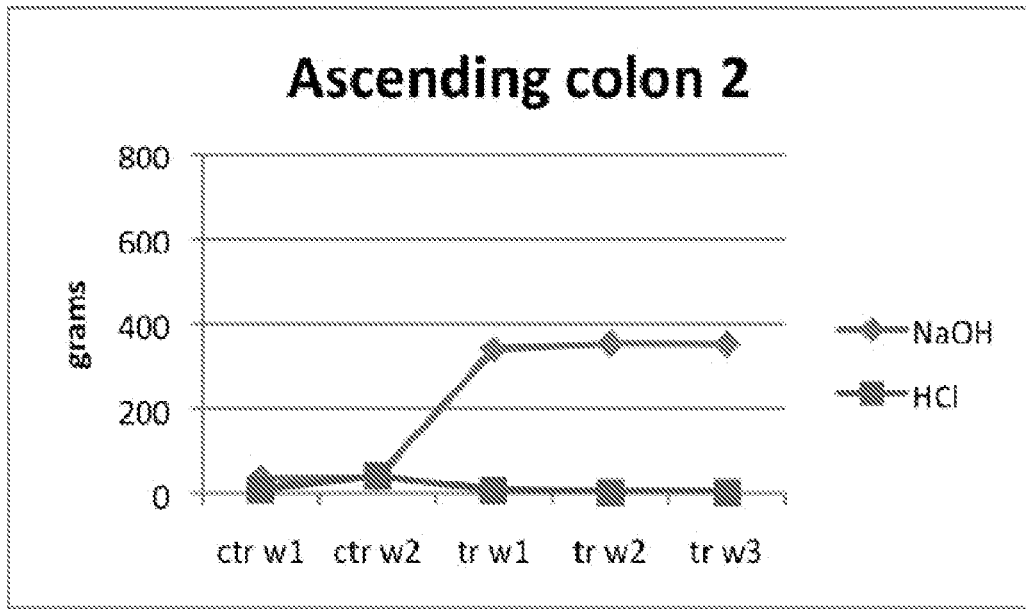
Figure 8C:
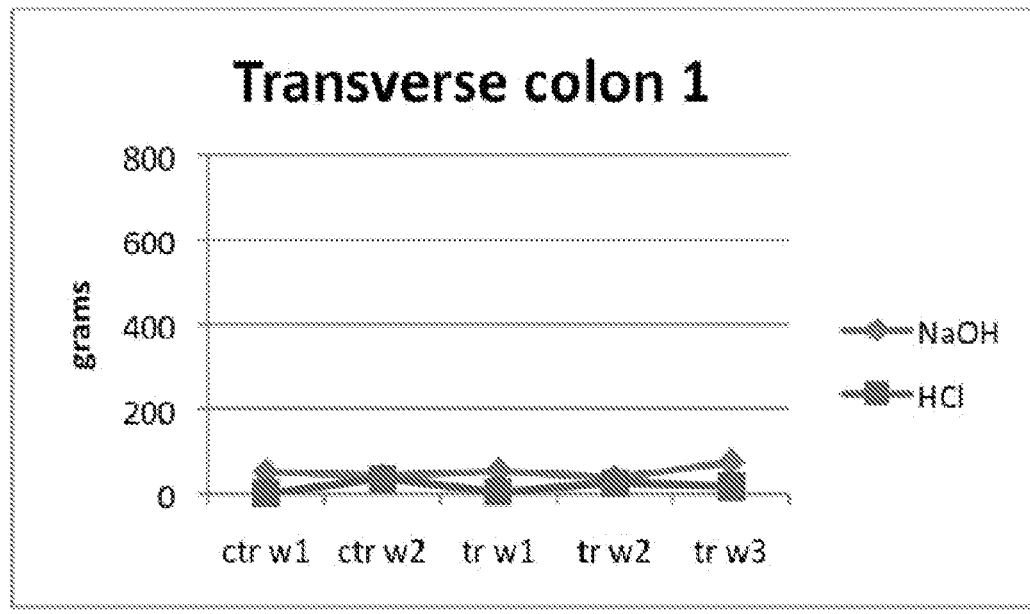
Figure 8D:
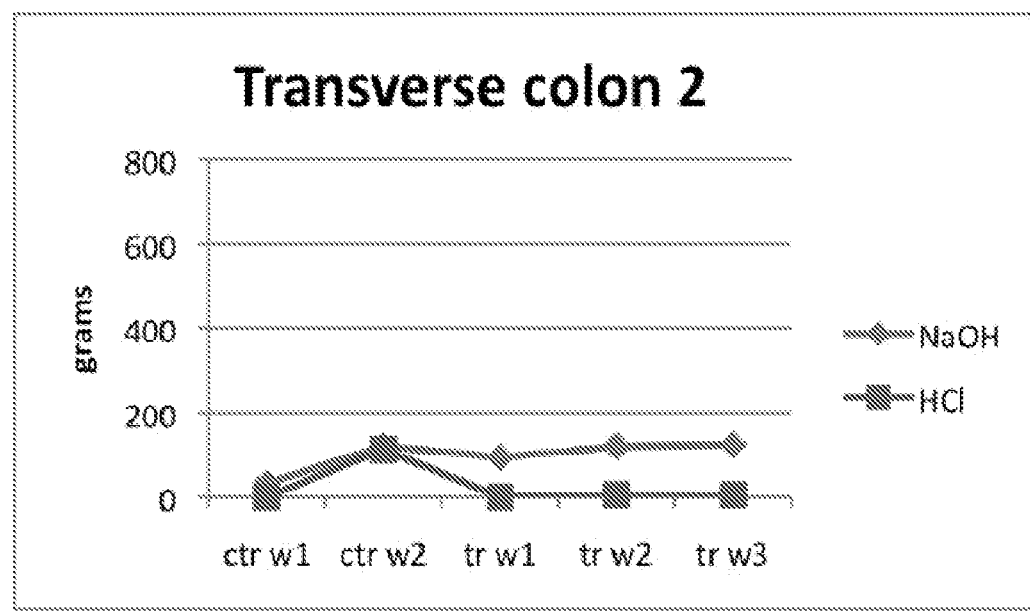
Figure 8E:
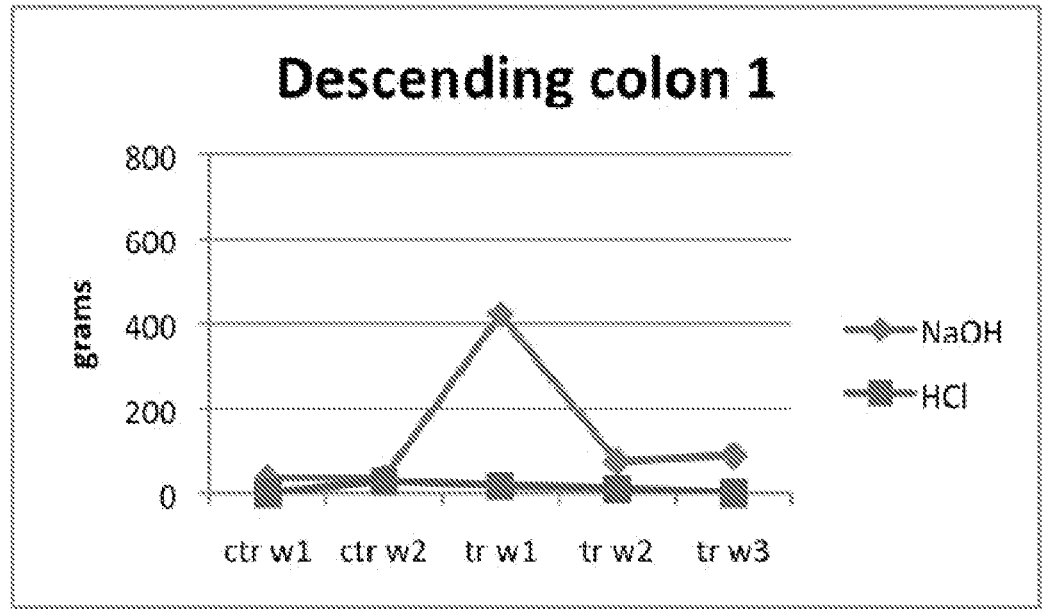
Figure 8F:
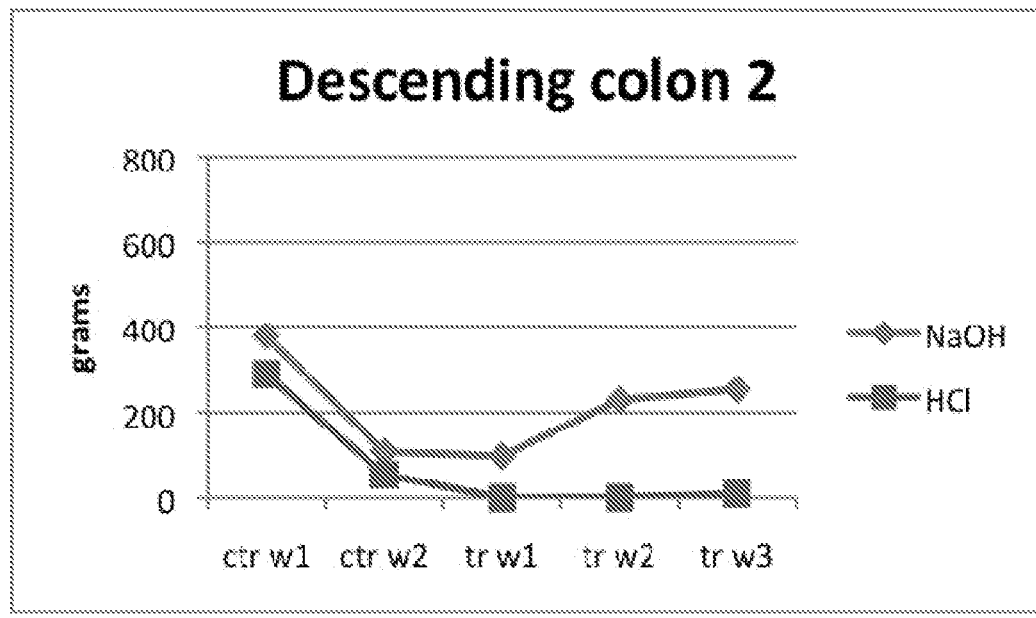

The human intestine harbors both lactate-producing and lactate-utilizing bacteria. Lactate is produced by lactic acid bacteria and decreases the pH of the environment acting also as an antimicrobial agent. It can also be rapidly converted to acetate, butyrate, and propionate by other microorganisms. For purposes of the instant study, samples were collected 3 times per week from all colon compartments. The analysis of lactate concentrations in the different colon regions throughout the course of the experiment is presented in FIGS. 7A and 7B.

Administration of both blends significantly increased remaining lactate concentrations in the ascending colon. Comparison of both SHIME runs shows that partial replacement of inulin and FOS decreases remaining lactate concentrations. This may relate to a more rapid and intense fermentation of inulin and FOS in the ascending colon as compared to acacia gum. The higher lactate concentrations in SHIME 1 are also consistent with the higher butyrate concentrations as lactate is an important precursor of butyrate.

Online pH Variation in the TWINSHIME

To make sure that optimal environmental conditions are maintained, the pH in a SHIME system is controlled by pH controllers in the following ranges: (i) 5.6-5.8 (ascending colon, "AC"), (ii) 6.2-6.4 (transverse colon, "TC"), and (iii) 6.6-6.8 (decending colong, "DC"). However, upon stabilization of the microbial community in the different reactors (starting from two weeks after inoculation), the microbial community can auto-regulate itself and acid-base consumption is normally low. During a treatment however, when bacteria adapt to the test product and produce for instance increased amounts of SCFA, the environment in the reactors may acidify, which results in additional pH control by means of more administration of base to the respective reactors. In this context, the degree of acidification during the experiment can be used as a measure of the intensity of bacterial metabolism of the prebiotic blend.

The analysis of acid and base consumption in the different colon regions throughout the course of the experiment is presented in FIG. 8. As shown by FIG. 8, administration of both blends induced acidification of the simulated colon reactors, indicative of increased SCFA production and of a healthier intestinal environment. However, whereas this acidification was limited to the ascending colon for Blend$^1$, acidification occurred throughout the entire simulated colon upon administration of Blend$^{1+}$. This shows that partial replacement of FOS and inulin by acacia gum changes the intestinal fermentation profile from a boost fermentation in the proximal colon into a more gradual fermentation in the complete colon.

Regarding the pH profile in TC1 and DC1, it was expected to obtain similar pH profiles. No immediate explanation is available for the observed difference. However, it is believed that the difference may be related to differences in buffering capacity of the two colon compartments.

Gas Production and pH Variation in Batch Experiments

The evaluation of total gas production is an important aspect related to potential tolerance issues for the two blends of this study. However, online total gas production measurements are difficult in continuous models of the gut, due to continuous in- and outflow of gasses. For this reason, the evaluation of the total gas production and the measurement of changes in $CO_2$ concentration have been conducted in batch setups. With respect to gas analysis, an additional batch test was conducted to measure estimate the total gas production and the gas phase composition under simulated colonic conditions.

Figure 9:
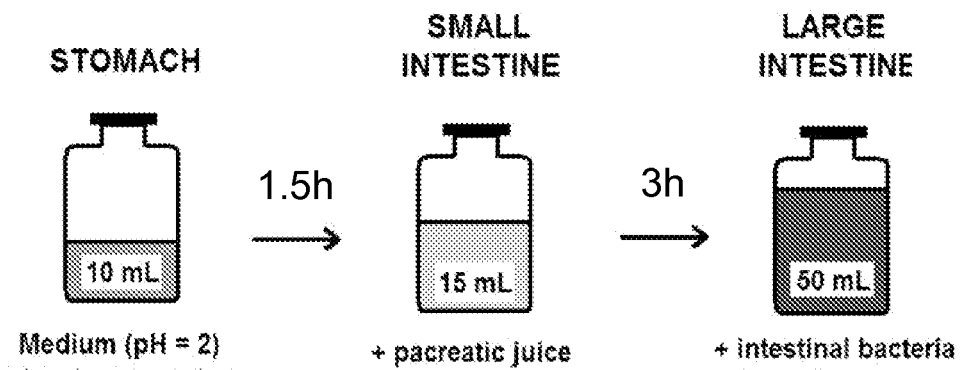
FIG. 9 shows a short-term screening assay consisting of the sequential incubation of a representative dose of the selected compound under simulated conditions for stomach, small intestine and ascending colon.

The typical short-term screening assay (FIG. 9), consists of the sequential incubation (in triplicate) of a representative dose of the selected compound under simulated conditions for (i) the stomach (pH 2, pepsin), (ii) the small intestine: addition of pancreatic enzymes and bile salts, and (iii) the large intestine with a representative bacterial inoculum in basal medium. This bacterial inoculum derived from an already 'in vitro adapted' microbial community from the ascending colon compartment in the SHIME system.

Figure 10:
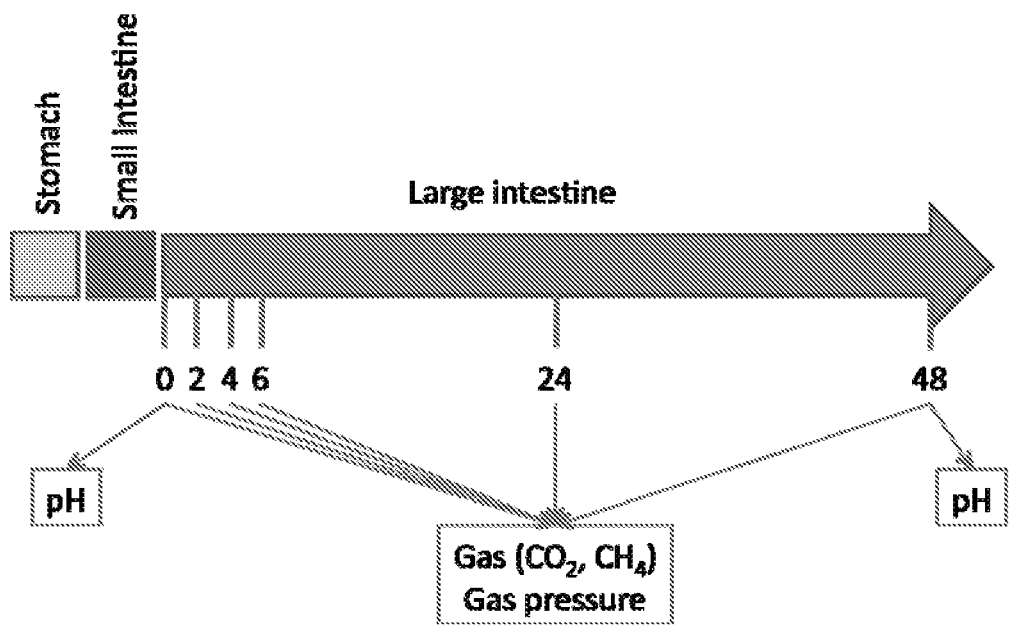
FIG. 10 shows a scheme of the batch experiment sampling for pH and gas measurements.
Figure 11A:
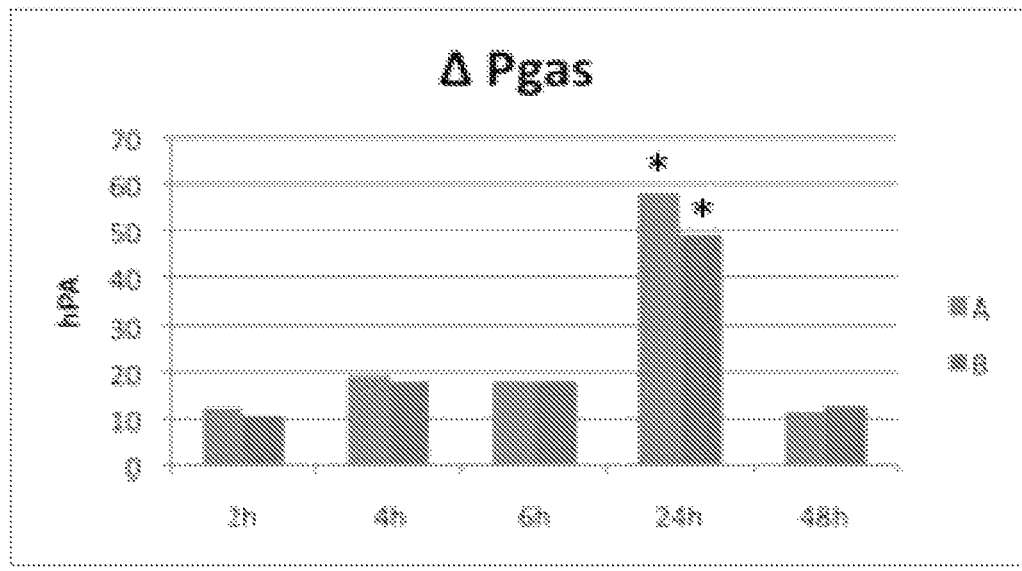
FIGS. 11A-11B show the change in total gas and $CO_2$ productions in the batch experiment. Blend[1] is designated as "A", Blend$^{1+}$ is designated as "B." Significant differences (as compared with previous sampling points) have been assessed by means of a Student's two-tailed Ttest and are indicated with * for P<0.05.
Figure 11B:
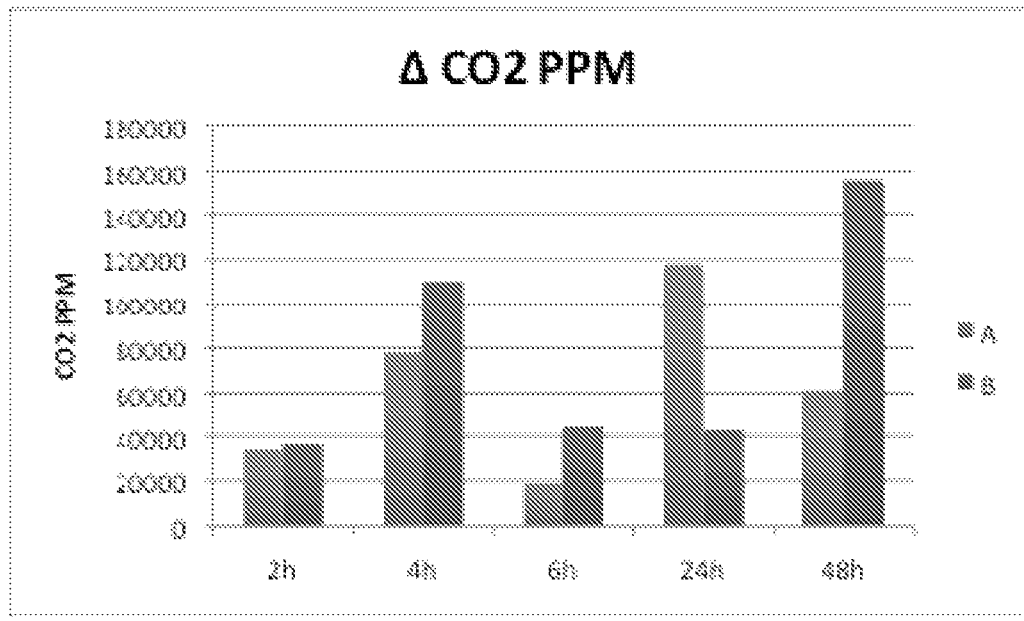

The experiment was designed in such a way that typical residence times of food products in the gastrointestinal tract are maintained. The scheme of the sampling is reported FIG. 10. The analysis of total gas production and composition—according to the scheme reported in FIG. 10—is presented in FIGS. 11A and 11B.

Gas production typically follows a Gaussian pattern. Even though it appears that a big jump occurred between 6 and 24 hours, which would be inconsistent with such a pattern, this is only due to the fact that no samples could be collected between 6 and 24 hours. As the major fraction of the administered fibers are fermented between 6 and 24 hours, a large apparent peak in gas production was observed at 24 hours. Comparison of both SHIME models shows that Blend$^{1+}$ fermentation induced a lower gas production as compared to the original Blend$^1$ even if this difference between the two products after 24 hours is not statistically significant.

$CO_2$ production (normally between 5 and 30% of the total gas in the gut according to Babb, R R, "Intestinal Gas (Medical Information)," West J. Med. 127: 362-363 (1977)) confirmed that Blend is fermented in a slower way (fermentation still occurs between 24 and 48 hours). This further confirms previous findings: partial replacement of FOS and inulin by acacia gum changes the intestinal fermentation profile into a more gradual fermentation.

Figure 12:
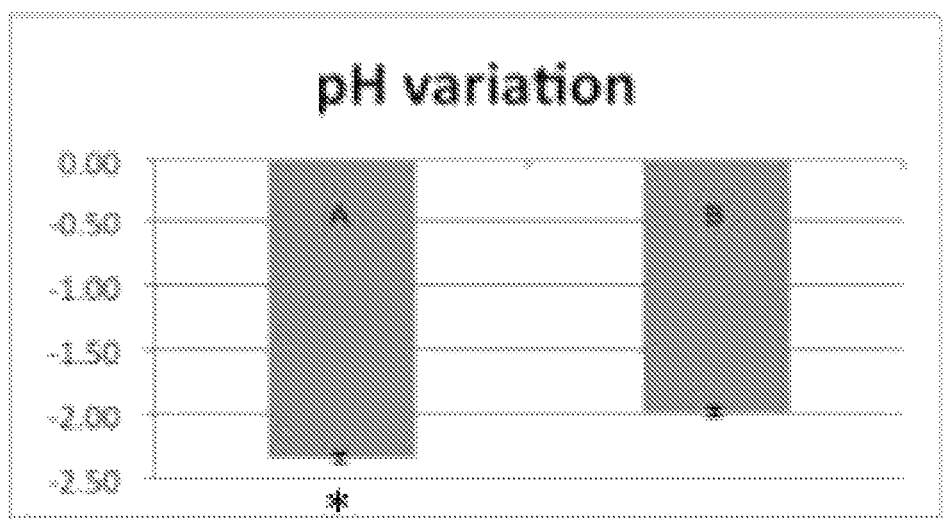
FIG. 12 shows the change in pH in the batch experiment comparing the values at time 0 hours and 48 hours. Blend$^{1}$ is designated as "A", Blend$^{1+}$ is designated as "B." Significant differences (as compared with the other product) have been assessed by means of a Student's two-tailed Ttest and are indicated with * for P<0.05.
Figure 13A:
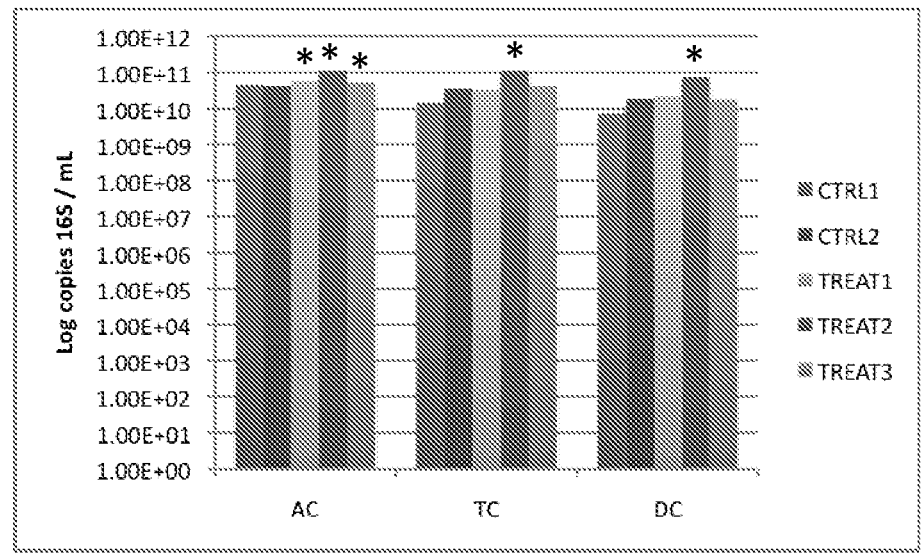
FIGS. 13A-13B show qPCR data for the total bacteria presented per experimental week in each colon compartment.
Figure 13B:
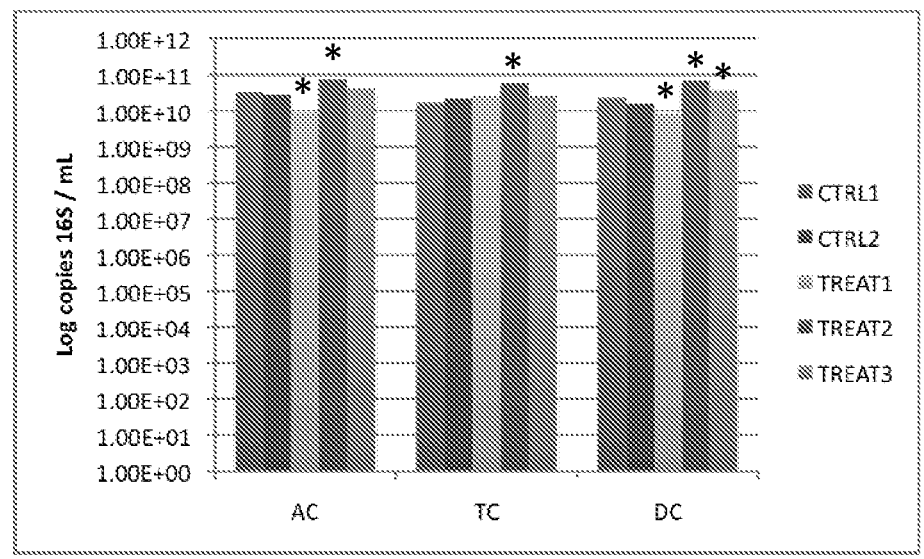
Figure 14A:
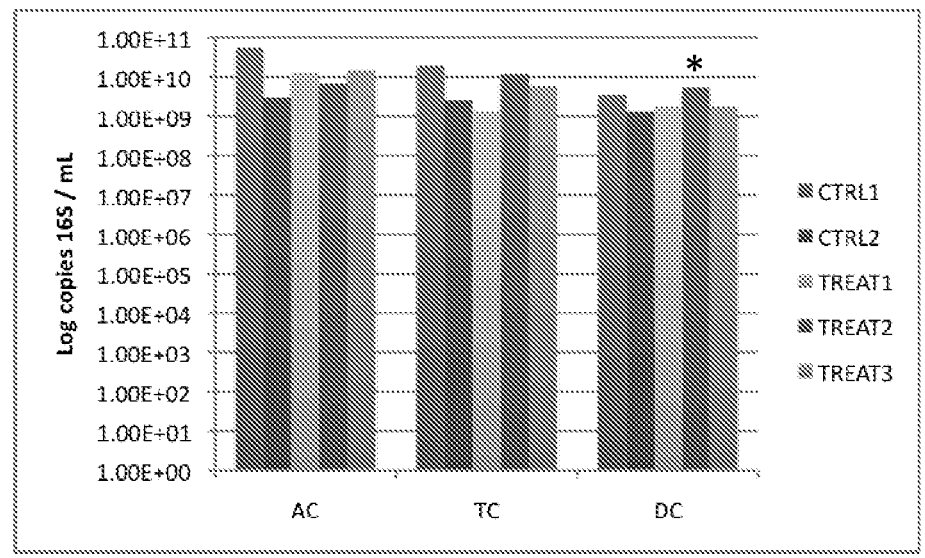
FIGS. 14A-14B show qPCR data for the total Bacteriodetes presented per experimental week in each colon compartment.
Figure 14B:
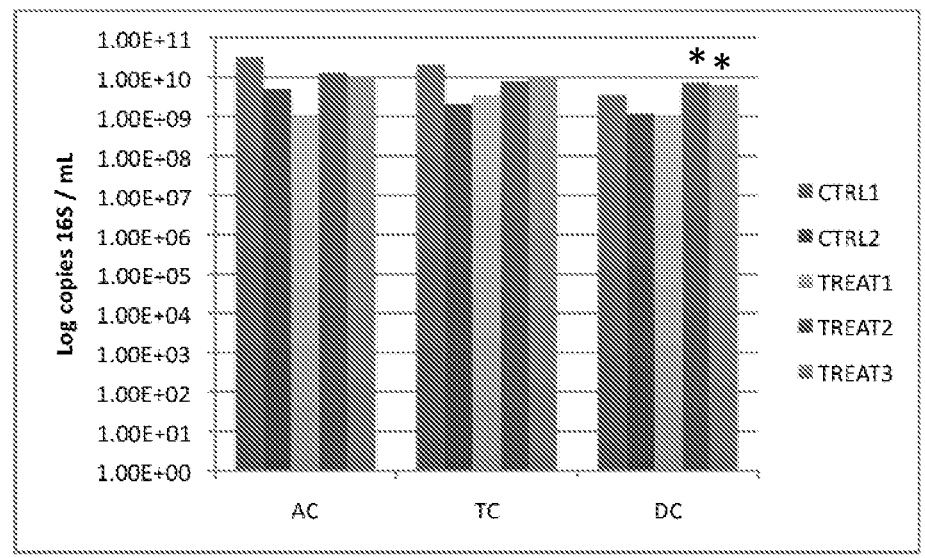
Figure 15A:
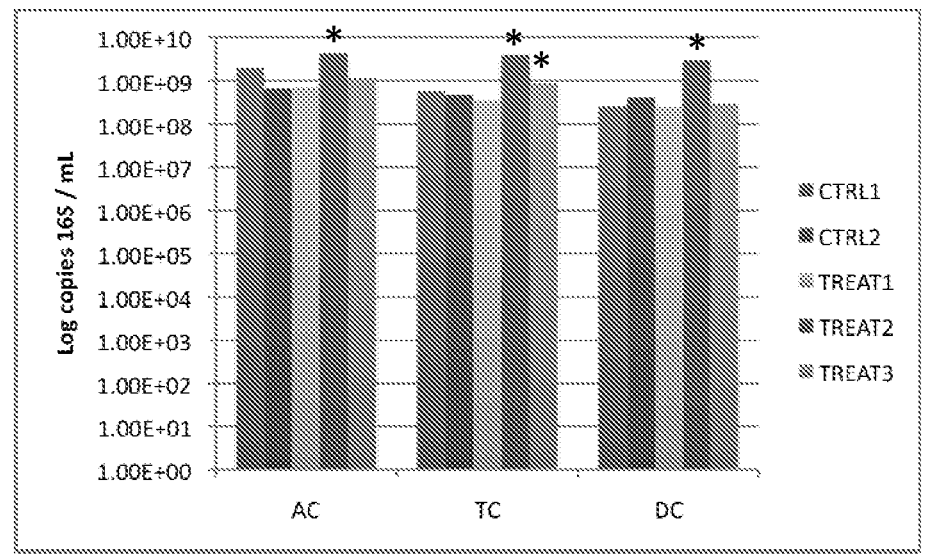
FIGS. 15A-15B show qPCR data for the total Firmicutes presented per experimental week in each colon compartment.
Figure 15B:
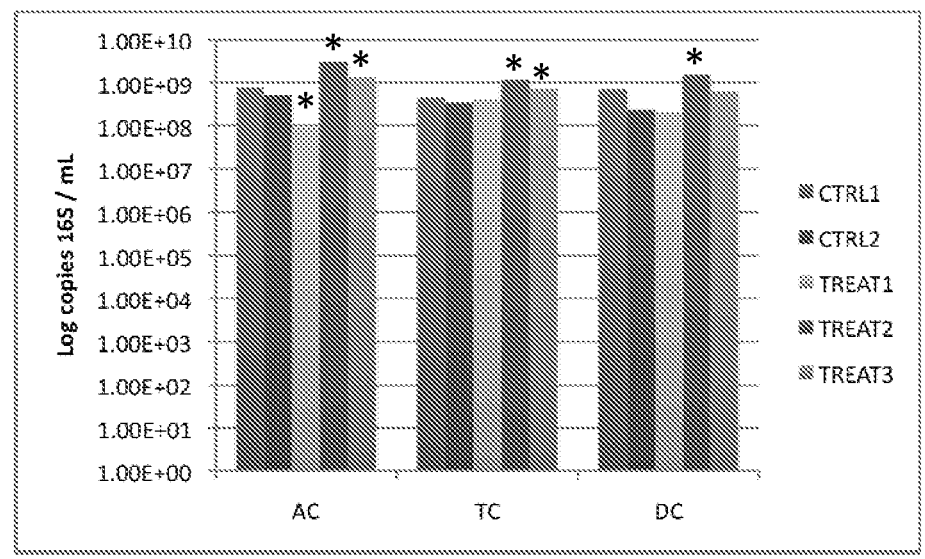
Figure 16A:
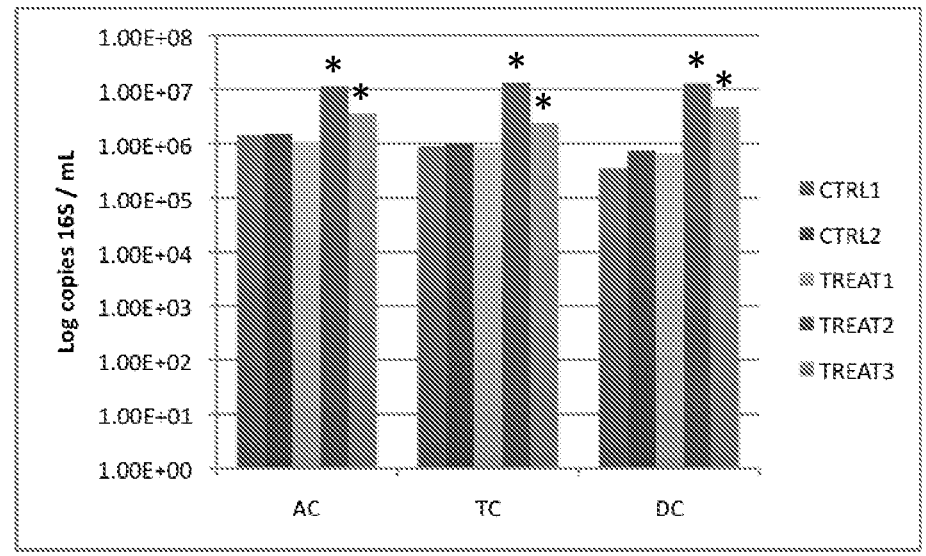
FIGS. 16A-16B show qPCR data for the total *Lactobacilli* presented per experimental week in each colon compartment.
Figure 16B:
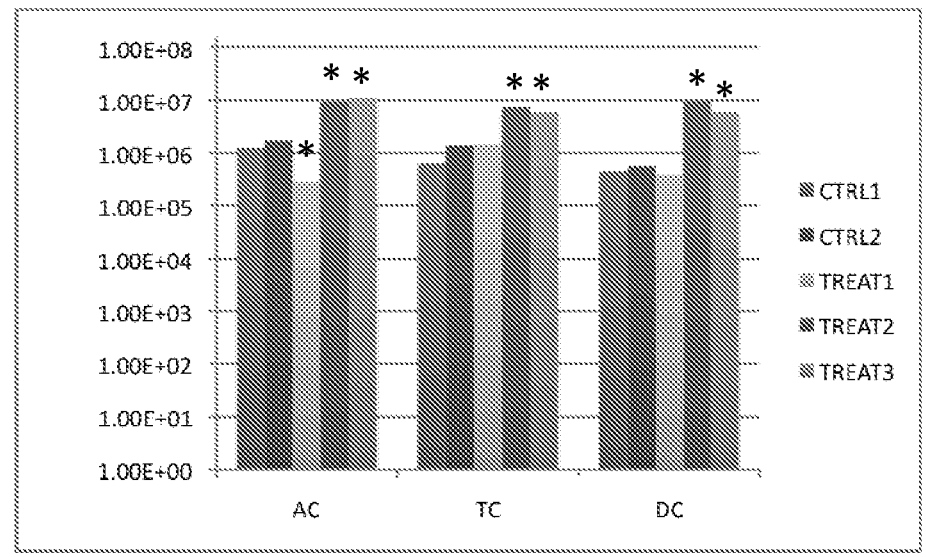
Figure 17A:
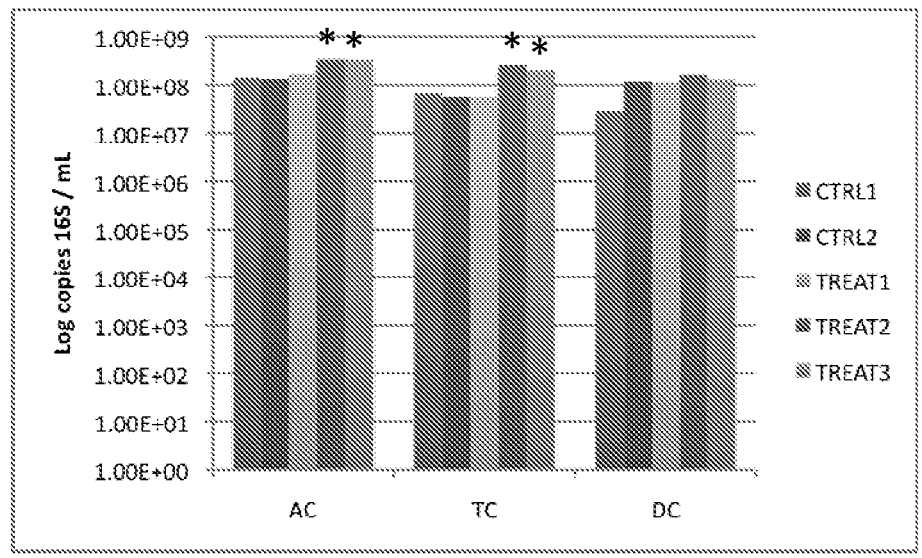
FIGS. 17A-17B show qPCR data for the total *Bifidobacteria* presented per experimental week in each colon compartment.
Figure 17B:
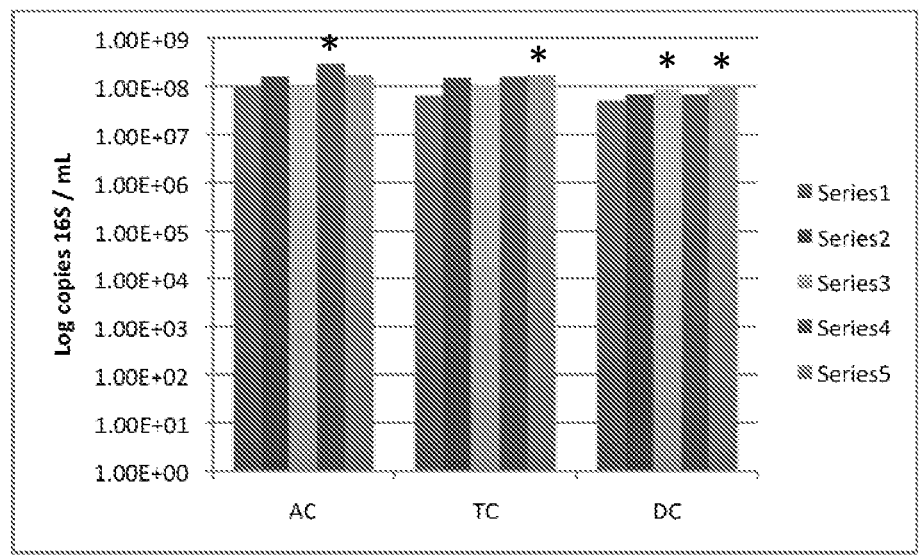

As already stated above, the degree of acidification at the end of the experiment is a measure of the intensity of bacterial metabolism of the potential prebiotic. The pH of medium in the batch incubations was therefore determined at the beginning and at the end of the experiment to confirm the data obtained with the online measurement (FIG. 12). The ΔpH in the batch experiment again confirms that Blend$^1$ is fermented faster than Blend$^{1+}$.

Analysis of the Microbial Community Composition

Samples were collected once per week from each colon compartments of the TWINSHIME to evaluate the effect of the treatment on the luminal microbial community composition by means of quantitative polymerase chain reaction ("qPCR") and to analyze the mucosa-associated microbial community by means of plate counting.

Luminal Microbial Community Composition qPCR was used to monitor total bacteria, bifidobacteria, lactobacilli, firmicutes, and bacteroidetes. qPCR is a molecular technique which is based on the amplification of specific bacterial sequences (165 rRNA genes), combined with the quantification of the number of these specific sequences in the microbial ecosystem at different time points. As this technique is not dependent on the (lack of) culturability of the bacteria, data generated with this method offer a more reliable overview on quantitative effects on the microbial community, due to the prebiotic treatment.

Administration of both blends resulted in a clear increase of *Lactobacilli* in all colon compartments and significant increase in *Bifidobacteria* in the ascending and transverse colon. Blend$^{1+}$ also induced a small, but significant increase in *Bifidobacteria* in the descending colon. On top of this, administration of both blends increased the counts of the dominant bacterial populations (total bacteria and Firmicutes). Blend$^{1+}$ also induced an increase in Bacteroidetes in the descending colon.

Firmicutes and Bacteroidetes are the two most dominant bacterial bacterial phyla in the gut. Bacteroidetes are considered as very important saccharolytic fermenting bacteria, as a large part of the proteins codified by Bacteroidetes goes to breaking down polysaccharides and metabolizing their sugars. Some species belonging to this group are also associated with propionate production. The increased concentration of Bacteroidetes in the descending colon upon Blend$^{1+}$ administration is therefore a further confirmation of the more gradual fermentation of acacia gum, leading to increased saccharolytic fermentation in the distal colon.

Firmicutes are users of the metabolic intermediates produced by the metabolism of Bacteroidetes. They include *Lactobacilli* and *Clostridia*. The latter are often considered as negative for health as specific *clostridia* are well-known pathogens. Yet, among the *Clostridia* are also several of the most important butyrate producers, a bacterial metabolite which is considered as a key health beneficial compound.

FIGS. 13A-B through FIGS. 17A-B show qPCR data from each bacterial group presented per experimental week in each colon compartment. All of FIGS. A relate to Blend$^1$, while all of FIGS. B related to Blend$^{1+}$.

Figure 18A:
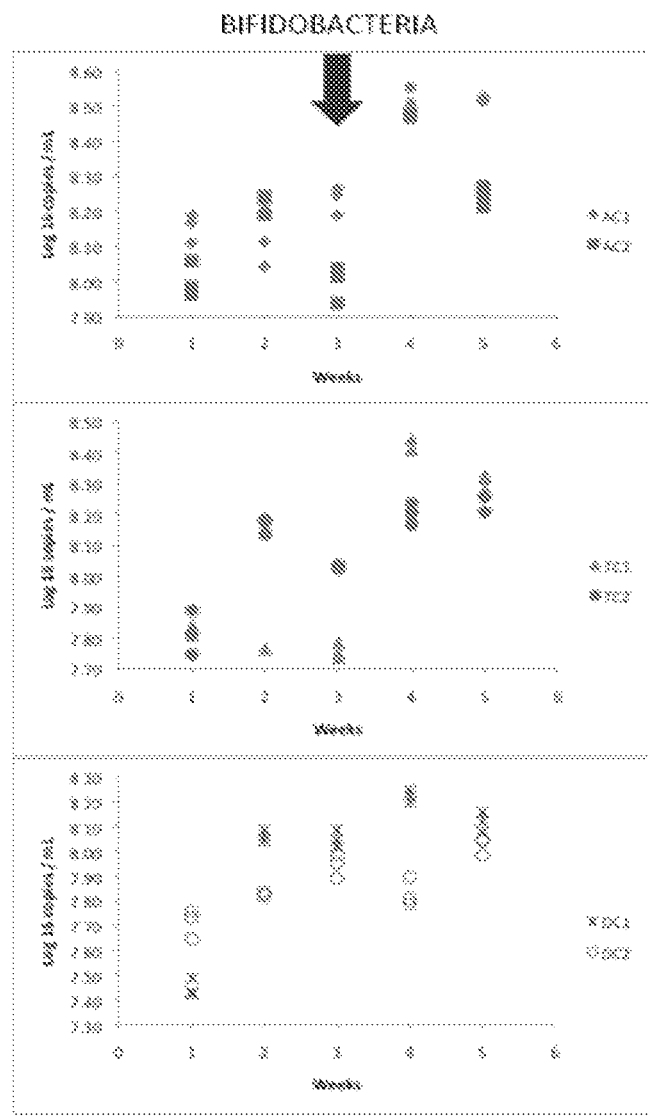
FIGS. 18A-18B illustrate comparisons of the data of each colon vessel for the two products in a scatter plot. AC1, TC1, and DC1 refer to Blend$^{1}$; AC2, TC2, and DC2 refer to Blend$^{1+}$. Weeks 1-2 were the control period and weeks 3-5 were the treatment period. The red arrow indicates for each group the position of the knot in the spline model.
Figure 18B:
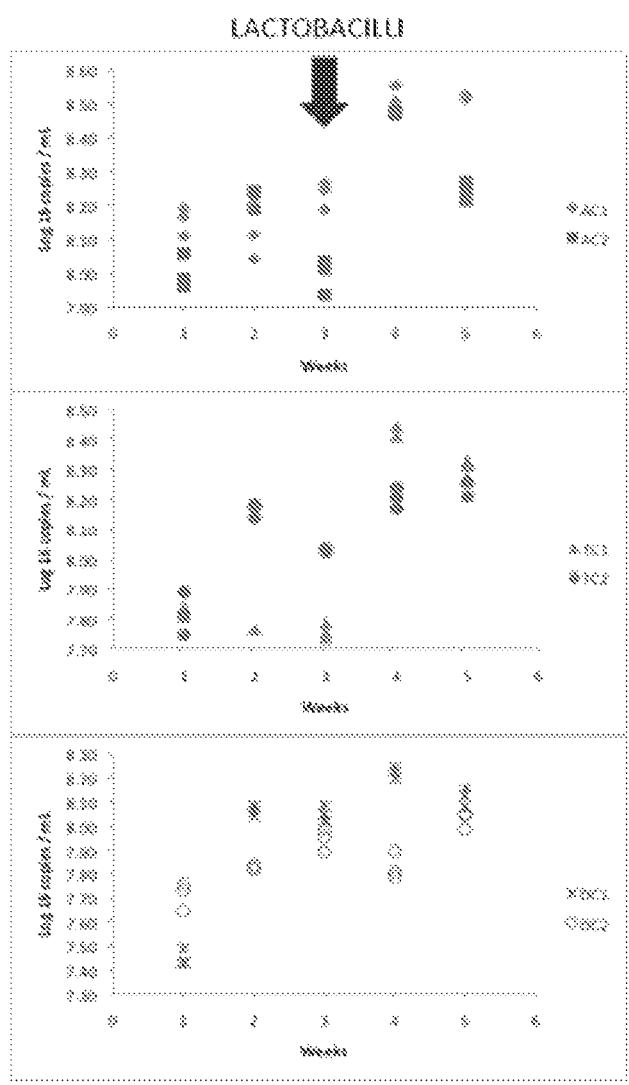
Figure 19A:
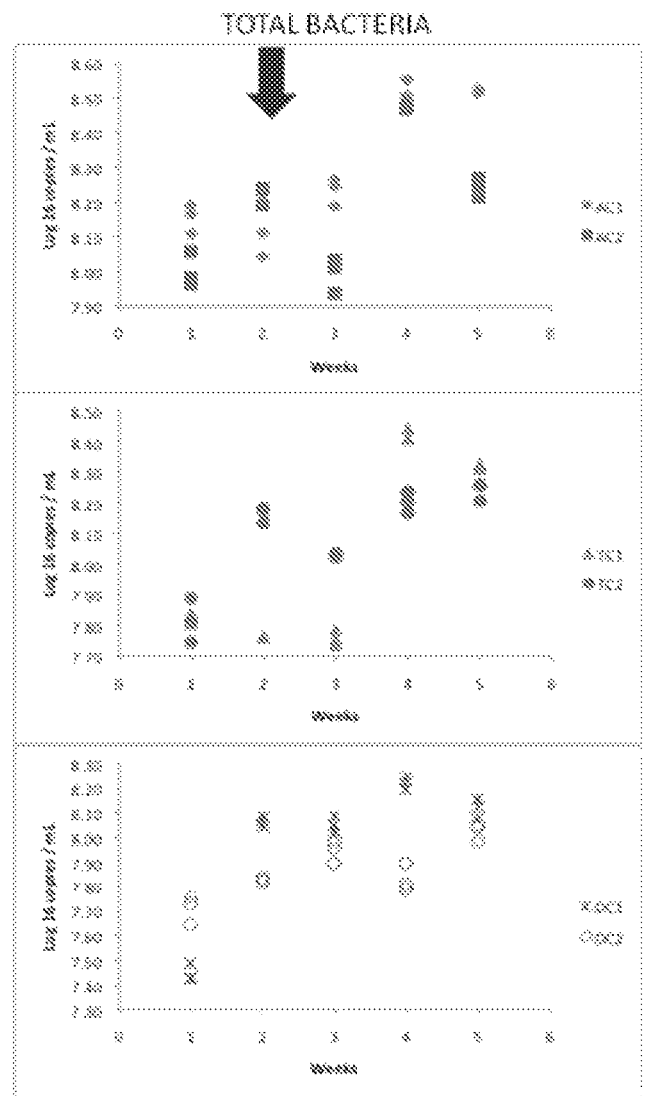
FIG. 19A-19B illustrate comparisons of the data of each colon vessel for the two products in a scatter plot. AC1, TC1, and DC1 refer to Blend$^{1}$; AC2, TC2, and DC2 refer to Blend$^{1+}$. Weeks 1-2 were the control period and weeks 3-5 were the treatment period. The red arrow indicates for each group the position of the knot in the spline model.
Figure 19B:
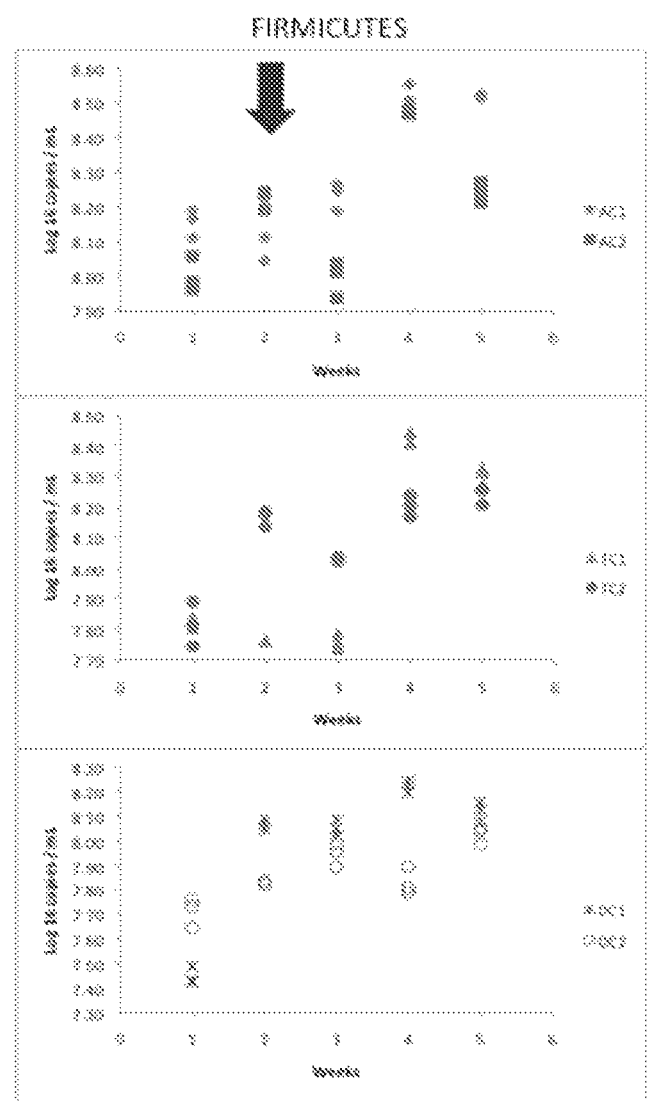
Figure 20:
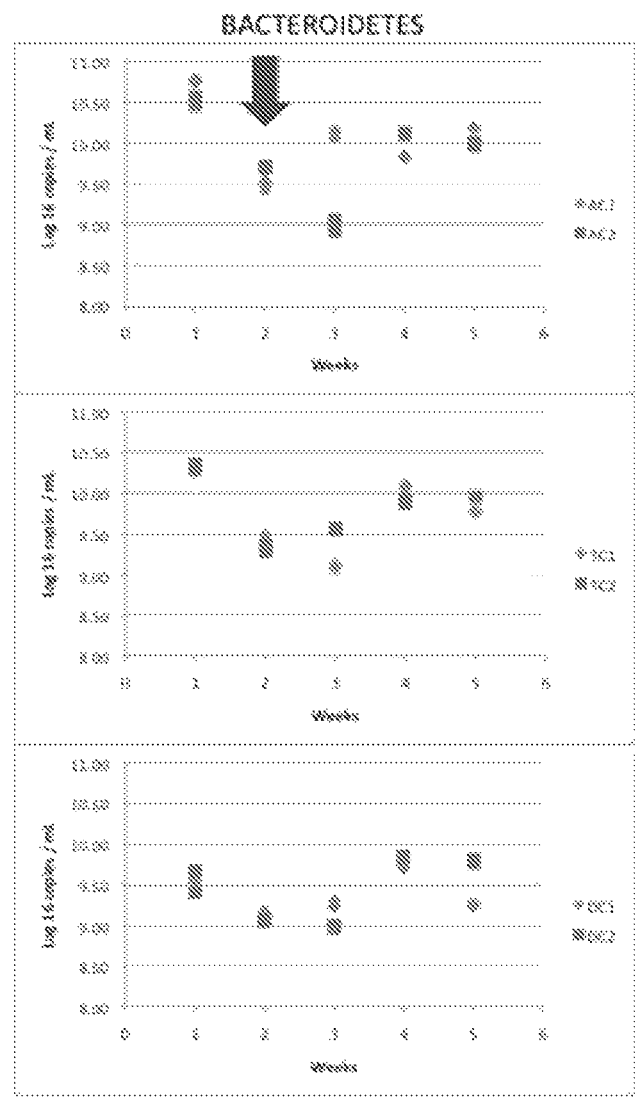
FIG. 20 is a comparison of the data of each colon vessel for the two products in a scatter plot. AC1, TC1, and DC1 refer to Blend$^{1}$; AC2, TC2, and DC2 refer to Blend$^{1+}$. Weeks 1-2 were the control period and weeks 3-5 were the treatment period. The red arrow indicates for each group the position of the knot in the spline model.

To compare the effect of the two products on the different bacterial groups we applied a longitudinal statistical approach that allowed to evaluate the different trends induced by the treatments. A linear spline model, changing the position of the knot on the second or third week (depending on the extent of delay in the treatment effect—indicated with a red arrow in FIGS. 18A, 18B, 19A, 19B and 20) was used to fit the data and to analyze the control vs. the treatment period. The approach is based on the creation of a complex model and the subsequent removal, step by step, of different predictors. The difference of the maximum likelihood values of two equations compared with the respective Chi Square provides information regarding whether the removed predictor had a statistical significance or not. In FIGS. 18-20, the comparison of the data from each colon vessel for the two products are presented in a scatter plot. AC1, TC1 and DC1 always refer to Blend$^1$; AC2, TC2 and DC2 refer to Blend$^{1+}$. Weeks 1-2 represent a control period, while weeks 3-5 represent a treatment period. Below each figure the statistical interpretation of the trend is discussed.

As shown by FIGS. 18A and 18B, both blends showed bifidogenic properties. FIG. 18A demonstrates that the increase in *Bifidobacteria* induced by Blend$^1$ is statistically higher than Blend$^{1+}$. It is known from literature that both FOS and inulin can enhance *Bifidobacteria* concentrations in the human gut, yet partial replacement by acacia gum still increased *Bifidobacteria*, confirming that this replacement has no negative consequences for its prebiotic activity. Moreover, as shown in FIG. 18B, Blend$^{1+}$ induced a higher increase in *Lactobacilli* in the ascending colon as compared to Blend$^1$.

FIGS. 19A and 19B illustrate that, based on the profiles for total bacteria, a decrease in the 165 rRNA genes copy number could be observed for Blend$^{1+}$ in the ascending colon during the first week of treatment. This decrease mainly correlates with the decrease of the dominant Firmicutes and Bacteroidetes phyla in the same colon compartment. This could be explained by the fact that acacia gum is more selective and specific to ferment as compared to FOS and inulin and that the bacteria need a longer time to adapt to Blend$^{1+}$. Statistically, Blend$^1$ induced also higher Firmicutes concentrations in the transverse colon.

As shown in FIG. 20, the amount of Bacteroidetes in the ascending colon of the SHIME treated with Blend[1+] is statistically lower than Blend[1] during the first week of treatment, as already explained above. In the remaining part of the colon there are no differences in the effect generated by the two products.

Mucosa-Associated Microbial Community

Specific bacteria-host interactions and modifications in this process due to a given treatment are now considered as one of the most important factors determining health effects of prebiotic fibers. The human intestinal tract harbors a large and complex community of microbes which is involved in maintaining human health by for instance preventing colonization by pathogens and by producing important nutrients. Microorganisms are not randomly distributed throughout the intestine and those adhering to the gut wall play an important role as they instruct mucosal immune responses and occupy a niche at the expense of potentially harmful colonizers (pathogens). As this interaction is very difficult to study in vivo due to problems with accessibility and complexity, ProDigest and LabMET (UGent) recently developed an innovative in vitro toolbox to evaluate whether a prebiotic has the capacity to enhance the adhesion of health promoting bacteria to the gut wall. This assay includes the investigation of the attachment of the intestinal microbial community from specific colon regions using samples taken from the SHIME reactor at different time points and the quantification of different bacterial groups within the attached community (total anaerobes, *Clostridia, Bifidobacteria, Lactobacilli*, and fecal coliforms). Data is then processed to calculate the so-called Adhesion Related Prebiotic Index (AR-PI) (see, Van den Abbeele et al., "In vitro model to study the modulation of the mucin-adhered bacterial community," *Appl. Microbiol. Biotechnol.* (2009)) according to the following formula:

$$AR-PI = \frac{\frac{bif_{80}}{bif_{80,c}} + \frac{lac_{80}}{lab_{80,c}} - \frac{col_{80}}{col_{80,c}} - \frac{clos_{80}}{clos_{80,c}}}{\frac{Tot_{80}}{Tot_{80,c}}}$$

Table 7 shows the AR-PI calculated taking into account the average values from the control and treatment period.

| | AR-PI-TREAT | | |
|---|---|---|---|
| | AC | TC | DC |
| SHIME 1 | 8.7 | −0.4 | −0.7 |
| SHIME 2 | −2.7 | −7.5 | −2.1 |

In this specific case, it is not possible to apply a particular statistic because the measurements were single measurements and these values were compared within the same formula. It is believed that a variation of the index±1 is biologically not significant. Considering Table 7, Blend[1] (which is rapidly fermented) had an immediate effect on the AR-PI in the AC and no effect in the last two colon compartments. On the contrary, Blend[1+] exerted an effect all along the colon.

In Table 8, the AR-PI is presented separately for each week of the treatment by comparing the single weeks of treatment with the average of the control period. For each value, additional information is also provided to explain the changes in the AR-PI in relation to the observed variation in the investigated bacterial groups.

| | AR-PI-TREAT | | | | | | | | |
|---|---|---|---|---|---|---|---|---|---|
| | AC | | | TC | | | DC | | |
| | Tr1 | Tr2 | Tr3 | Tr1 | Tr2 | Tr3 | Tr1 | Tr2 | Tr3 |
| SHIME 1 | 28.19 | 8.67 | 1.96 | −4.99 | −0.68 | 11.08 | −0.46 | 0.38 | −1.07 |
| SHIME 2 | −2.43 | −0.02 | −0.22 | −27.49 | −7.35 | −6.06 | −2.12 | 0.21 | −1.40 |

A general consideration: within the formula *Clostridium* spp. are considered as negative bacteria. However, as discussed above, among *Clostridia* there are several bacteria involved in SCFA metabolism. Therefore, the suggestion is to interpret the value of the AR-PI also in terms of which bacterial groups are enhanced and not only if the value is positive or negative.

Several conclusions may be drawn from the information represented in Table 8. First, it is clear that Blend[1] is mainly fermented in the proximal colon and exerts an effect on the AR-PI in the ascending colon. During the second and third week bacteria start to adapt to the product. Also, in the transverse colon the bacteria are positively affected by Blend[1] but it takes the full treatment period to observe this effect. Blend[1] did not induce any change in the distal colon. Blend[1+] is probably a more balanced and less easy fermentable formulation. For this reason it exerts an effect all over the colon. The numbers are always negative and this is mainly correlated to an increase of *Clostridia* and a parallel decrease in *Bifidobacteria*.

All these analyses were performed using plate counts for the specific groups. As we also analyzed the luminal content by plate counts as part of the adhesion experiment, these data are also available. Hence, a secondary outcome of the analyses is also the quantification of the luminal content of *Clostridia* and *Coliforms*. These data are reported in Table 9.

TABLE 9

Concentrations (CFU/mL) of Clostridia and Coliforms for tests performed using Blend[1] (SHIME 1) and Blend[1+] (SHIME 2) for 5 weeks of the SHIME experiments. Values are compared to those of the second week of control: those in red are higher, white are within the same range, and green are lower.

| SHIME 1 | | | | | |
|---|---|---|---|---|---|
| | CTR W1 | CTR W2 | TREAT 1 | TREAT 2 | TREAT 3 |
| Clostridia AC | 2.17E+07 | 1.14E+07 | 8.84E+07 | 3.35E+07 | 1.16E+07 |
| Coliforms | 1.11E+08 | 2.42E+08 | 8.11E+07 | 7.77E+07 | 2.90E+07 |
| Clostridia TC | 5.49E+06 | 1.27E+07 | 8.97E+07 | 1.80E+07 | 1.02E+07 |
| Coliforms | 3.17E+07 | 1.20E+08 | 1.04E+08 | 2.30E+07 | 5.59E+06 |
| Clostridia DC | 1.55E+07 | 1.60E+07 | 3.84E+07 | 7.42E+06 | 8.54E+06 |
| Coliforms | 2.07E+07 | 4.87E+07 | 2.91E+07 | 1.30E+07 | 1.77E+07 |

TABLE 9-continued

Concentrations (CFU/mL) of Clostridia and Coliforms for tests performed using Blend[1] (SHIME 1) and Blend[1+] (SHIME 2) for 5 weeks of the SHIME experiments. Values are compared to those of the second week of control: those in red are higher, white are within the same range, and green are lower.

| | | SHIME 2 | | | | |
|---|---|---|---|---|---|---|
| | | CTR W1 | CTR W2 | TREAT 1 | TREAT 2 | TREAT 3 |
| Clostridia | AC | 1.69E+07 | 6.45E+06 | 6.25E+07 | 2.17E+07 | 4.01E+07 |
| Coliforms | | 9.92E+07 | 8.65E+07 | 6.72E+07 | 4.11E+07 | 3.91E+07 |
| Clostridia | TC | 8.13E+06 | 3.70E+08 | 5.52E+07 | 1.79E+08 | 1.15E+07 |
| Coliforms | | 4.03E+07 | 7.81E+07 | 5.56E+07 | 4.23E+08 | 1.50E+07 |
| Clostridia | DC | 1.57E+07 | 4.43E+07 | 9.15E+07 | 3.63E+07 | 1.53E+07 |
| Coliforms | | 5.75E+07 | 1.41E+08 | 6.98E+07 | 4.09E+07 | 1.98E+07 |

Overall, Blend[1] induced an increase of both *Clostridia* and *Coliforms* in the proximal colon during the first week of treatment (except for *Coliforms* in the AC) but at the end of the treatment period the values are comparable or lower to those of the control period. The descending colon was not affected (this is in accordance with the fact that Blend[1] is mainly fermented in the first part of the colon). Blend induced a general decrease in *Clostridia* and *Coliforms* at the end of the treatment except for *Clostridia* in the ascending colon.

Conclusions

Both blends were well fermented, resulting in decreased production of the toxic ammonium. Partial replacement of FOS and inulin by AG (Blend[1+]) changes the intestinal fermentation from a boost fermentation in the proximal colon into a gradual fermentation in the complete colon, as shown by acidification of all colon parts and more gradual gas production. Replacement of FOS and inulin by AG induced differences in SCFA production. The butyrogenic effect of Blend[1] was higher. Blend[1+] induced higher propionate concentrations. Both blends showed bifidogenic properties. Partial replacement of FOS and inulin by acacia gum has no negative consequences for its prebiotic activity. Moreover, Blend[1+] induced a higher increase in *Lactobacilli* in the ascending colon as compared to Blend[1]. AG is more selective and specific to ferment as compared to FOS and inulin.

According to the scientific literature, inulin-type prebiotics, which include FOS, OF, and inulin, resist enzymatic digestion in the upper gastrointestinal tract with the result that they reach the colon virtually intact and undergo bacterial fermentation. These products are mainly bifidogenic but, according to some reports, also *Lactobacilli* growth can be stimulated. The effects they have on other gut organisms are less consistent. From a physiological point of view, these dietary fibers are fermented to a large extent by a wide variety of anaerobic bacteria (mainly *Bifidobacteria* and bacteroidetes) in the proximal colon, which results in an increase in bacterial biomass, an increase in fecal mass, a change in intracolonic pH, and production of SCFAs (mainly acetate, butyrate and propionate). AG, on the other hand, also reaches the colon intact and has mainly been correlated with increased number of *Bifidobacteria* and *Lactobacilli* and with a higher propionate production.

Microbial Community Activity

A few conclusions from the instant study regarding microbial community activity are summarized below.

Both products are well fermented and gave clear indications of prebiotic activity.

Administration of both blends induced acidification of the simulated colon reactors, which is indicative of increased SCFA production and of a healthier intestinal environment.

Partial replacement of FOS and inulin by acacia gum changes the intestinal fermentation profile from a boost fermentation in the proximal colon into a more gradual fermentation in the complete colon, as shown by (i) acidification of all colon compartments in case of Blend[1+] administration, which was also confirmed in the batch experiment, (ii) lower and more gradual gas production in case of Blend[1+] administration (batch experiment), and (iii) higher lactate concentrations in the ascending colon upon Blend[1] administration.

Partial replacement of FOS and inulin by acacia gum induced differences in bacterial SCFA production. The butyrogenic effect of Blend[1] was higher than Blend[1+] while Blend[1+] showed a higher propionate concentration (even if not always supported by statistics). This shows that although both blends had a very positive effect in terms of SCFA production (butyrate and propionate are considered health beneficial), the specific fermentation profile depended on the specific composition of the blends.

The good fermentation of the two products as well as the higher saccharolytic metabolism is also confirmed by a decreased ammonium production during the treatment period without statistical differences between the products.

Microbial Community Composition

A few conclusions from the instant study regarding microbial community composition are summarized below. qPCR was used as culture-independent technique to monitor total bacteria, *Bifidobacteria, Lactobacilli*, Firmicutes and Bacteroidetes.

Both blends showed bifidogenic properties. The increase in *Bifidobacteria* induced by Blend[1] is statistically higher than Blend[1+], yet partial replacement by acacia gum still increased *Bifidobacteria*, confirming that this replacement has no negative consequences for its prebiotic activity. Moreover, Blend[1+] induced a higher increase in *Lactobacilli* in the ascending colon as compared to Blend[1].

A decrease in total bacteria could be observed for Blend[1+] in the ascending colon during the first week of treatment. This decrease mainly correlates with the decrease of the dominant Firmicutes and Bacteroidetes phyla in the same colon compartment. This could be explained by the fact that acacia gum is more selective and specific to ferment as compared to FOS and inulin and that the bacteria need a longer time to adapt to Blend[1+].

Further, a prolonged treatment with both blends induced a decrease of *Clostridia* and *Coliforms* at the end of the treatment (Blend[1+]>Blend[1]).

Mucosa-Associated Microbial Community

Blend[1] is mainly fermented in the proximal colon and exerts an immediate effect on the AR-PI in the ascending colon. During the second and third week bacteria start to adapt to the product. Bacteria in the transverse colon were also affected but it takes the full treatment period to observe this effect. No effects were seen in the descending colon. Therefore, Blend[1+] is probably a more balanced and less easy fermentable formulation. For this reason it exerts an effect all over the colon.

In general, it can be seen that both blends exhibit prebiotic activity. Partial replacement of FOS and inulin by AG did not decrease the potential of Blend[1+], as shown by the increased production of the health beneficial SCFA propionate and butyrate, intestinal acidification and stimulation of both *Lactobacilli* and *Bifidobacteria*. In contrast, Blend[1+] acidified more gradually and throughout the complete simulated colon.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of promoting gut microbiota balance, the method comprising administering to an individual in need of such treatment an effective amount of a nutritional composition comprising a fructo-oligosaccharaide (FOS) in an amount of about 35 to about 44% by weight, a polysaccharide that is not partially hydrolysed guar gum (PHGG) in an amount of about 38% to about 50% by weight, inulin in an amount of 12 to 24% by weight; and the FOS and polysaccharide are present in a weight ratio of 62:38 to 38:62; and the FOS and inulin are present in a weight ratio of 82:18 to 58:42.

2. The method of claim 1, wherein the individual is undergoing medical treatments that lead to gastrointestinal tract disorders.

3. The method of claim 1, wherein the individual has experienced an illness or injury.

4. The method of claim 1, wherein the individual has experienced at least one.

5. The method of claim 1, wherein the promoting gut microbiota balance increases butyrate production in a patient's colon, the method increasing butyrate production compared to formulations that do not contain AG to produce cell proliferation in the colon and to lower colon pH to inhibit the growth of pathogenic bacteria.

6. The method of claim 5, wherein the butyrate production leads to a benefit selected from the group consisting of: anti-inflammatory benefits that help protect the patient's gut barrier; better mineral absorption, normalization of gastrointestinal transit time, and decrease in diarrhea.

7. The method of claim 1, wherein the promoting gut microbiota balance is a sustained shift over time in microbiota balance favoring beneficial bacteria.

8. The method of claim 7, wherein the beneficial bacteria is selected from the group consisting of *bifidobacteria, lactobacilli* and *bifidobacteria* and *lactobacilli*.

9. The method of claim 7, wherein pathogens are reduced.

10. The method of claim 9, wherein the pathogen is *clostridia*.

11. The method of claim 9, wherein *clostridia* is reduced in the distal colon.

12. The method of claim 1, wherein the promoting gut microbiota balance provides a health benefit selected from the group consisting of sustained fermentation, Small Chain Fatty Acid production, a shift in saccharlytic fermentation from ascending colon to descending colon leading to sustained carbohydrate fermentation in the descending colon and reduced protein fermentation, and combinations thereof, throughout the colon.

13. The method of claim 12, wherein there is a benefit selected from the group consisting of better nutrient reabsorption, water reabsorption, or electrolyte reabsorption, and combinations thereof.

14. The method of claim 12, wherein there is a benefit selected from the group consisting of improved gut regularity, improved constipation, improved diarrhea, improved irritable bowel syndrome, improved Crohn's disease, improved ulcerative colitis and combinations thereof.

15. The method of claim 12, comprising production of important short chain fatty acids, butyrate, proprionate, or combinations thereof.

16. The method of claim 12, wherein there is a benefit selected from the group consisting of a reduced pH, a preferred substrate for colonocytes, and better nutrient presentation to the colonocytes, throughout the entire length of the colon.

17. The method of claim 1, wherein the nutritional composition comprises DHA.

18. The method of claim 1, wherein the nutritional composition comprises an outer pea fiber.

* * * * *